United States Patent
Kulach et al.

(10) Patent No.: US 11,179,051 B2
(45) Date of Patent: *Nov. 23, 2021

(54) PULSE SPECTROSCOPY

(71) Applicant: Garmin Switzerland GmbH, Schaffhausen (CH)

(72) Inventors: Christopher J. Kulach, Calgary (CA); Paul R. MacDonald, Calgary (CA)

(73) Assignee: Garmin Switzerland GmbH

( * ) Notice: Subject to any disclaimer, the term of this patent is extended or adjusted under 35 U.S.C. 154(b) by 482 days.

This patent is subject to a terminal disclaimer.

(21) Appl. No.: 15/969,553

(22) Filed: May 2, 2018

(65) Prior Publication Data
US 2018/0317786 A1 Nov. 8, 2018

Related U.S. Application Data

(60) Provisional application No. 62/501,522, filed on May 4, 2017, provisional application No. 62/571,606, filed (Continued)

(51) Int. Cl.
*A61B 5/024* (2006.01)
*A61B 5/00* (2006.01)
(Continued)

(52) U.S. Cl.
CPC ...... *A61B 5/02427* (2013.01); *A61B 5/02416* (2013.01); *A61B 5/02438* (2013.01);
(Continued)

(58) Field of Classification Search
None
See application file for complete search history.

(56) References Cited

U.S. PATENT DOCUMENTS 5,431,170 A * 7/1995 Mathews ............. A61B 5/0002
600/323
5,524,617 A   6/1996 Mannheimer
(Continued)

FOREIGN PATENT DOCUMENTS

| EP | 3111834 A1 | 1/2017 |
| WO | 2015116891 A1 | 8/2015 |
| WO | 2017027551 A1 | 2/2017 |

OTHER PUBLICATIONS

U.S. Appl. No. 15/860,865, filed May 2, 2018, MacDonald.
(Continued)

*Primary Examiner* — Katherine L Fernandez
(74) *Attorney, Agent, or Firm* — Samuel M. Korte; Max M. Ali

(57) ABSTRACT

An electronic fitness device comprises a first optical transmitter, an optical receiver, and a processing element. The first optical transmitter is configured to transmit a first optical signal and a second optical signal. The optical receiver is configured to receive the first and optical signals and to generate first and second photoplethysmogram (PPG) signals resulting from the received optical signals. The processing element is configured to control the first optical transmitter to transmit the first optical signal the second optical signal, receive the first and second PPG signals from the optical receiver and compare them, identify a common cardiac component present in the first and the second PPG signals based on the comparison, determine a signal filter parameter based on the common cardiac component, and generate first and second cardiac components from the first and second PPG signals, respectively, based on the signal filter parameter.

12 Claims, 15 Drawing Sheets

Related U.S. Application Data on Oct. 12, 2017, provisional application No. 62/580,308, filed on Nov. 1, 2017, provisional application No. 62/580,024, filed on Nov. 1, 2017.

(51) Int. Cl.
*A61B 5/145* (2006.01)
*A61B 5/1455* (2006.01)

(52) U.S. Cl.
CPC ...... *A61B 5/14535* (2013.01); *A61B 5/14542* (2013.01); *A61B 5/14552* (2013.01); *A61B 5/4875* (2013.01); *A61B 5/681* (2013.01); *A61B 5/6824* (2013.01); *A61B 5/725* (2013.01); *A61B 5/7207* (2013.01); *A61B 5/7214* (2013.01); *A61B 5/7246* (2013.01); *A61B 5/7253* (2013.01); *A61B 5/7257* (2013.01); *A61B 5/7278* (2013.01); *A61B 5/7282* (2013.01); *A61B 5/0004* (2013.01); *A61B 2503/10* (2013.01); *A61B 2505/09* (2013.01); *A61B 2560/0462* (2013.01); *A61B 2562/0238* (2013.01); *A61B 2562/0242* (2013.01); *A61B 2562/04* (2013.01); *A61B 2562/043* (2013.01); *A61B 2562/046* (2013.01)

(56) References Cited

U.S. PATENT DOCUMENTS

| | | | |
|---|---|---|---|
| 5,632,272 A * | 5/1997 | Diab | A61B 8/5276 |
| | | | 600/323 |
| 9,292,008 B1 | 3/2016 | Ahamed et al. | |
| 2003/0109775 A1 | 6/2003 | O'Neil et al. | |
| 2011/0060200 A1 | 3/2011 | Bernreuter | |
| 2012/0209095 A1 | 8/2012 | Huiku | |
| 2013/0030267 A1 | 1/2013 | Lisogurski et al. | |
| 2014/0213863 A1 * | 7/2014 | Loseu | A61B 5/725 |
| | | | 600/324 |
| 2015/0065889 A1 | 3/2015 | Gandelman et al. | |
| 2015/0208950 A1 * | 7/2015 | Akl | A61B 5/02007 |
| | | | 600/324 |
| 2015/0313549 A1 | 11/2015 | Lee et al. | |
| 2016/0287107 A1 | 10/2016 | Szabados et al. | |
| 2016/0296174 A1 | 10/2016 | Isikman et al. | |
| 2018/0317785 A1 | 11/2018 | MacDonald et al. | |
| 2018/0317852 A1 | 11/2018 | MacDonald et al. | |
| 2018/0353134 A1 * | 12/2018 | Walter | A61B 5/6817 |

OTHER PUBLICATIONS

U.S. Appl. No. 15/969,574, filed May 2, 2018, MacDonald.
Casson et al., Gyroscope vs. accelerometer measurements of motion from wrist PPG, during physical exercise, School of Electrical and Electronic Engineering, The University of Manchester, Manchester, UK, ICT Express 2, 2016, p. 175-179.
Nitzan et al., Pulse oximetry: fundamentals and technology update, Dove Press journal, Medical Devices: Evidence and Research Jul. 8, 2014.
Nogawa et al., Development of an optical arterial hematocrit measurement method: pulse hematometry. Engineering in Medicine and Biology 27th Annual Conference, Sep. 1-4, 2005.
Wieben, O., Light Absorbance in Pulse Oximetry, published prior to Jan. 3, 2018.
Yadhuraj et al., Motion Artifact Reduction in Photoplethysmographic Signals: A Review, International Journal of Innovative Research & Development, Mar. 2013, vol. 2, Issue 3, p. 626-640.
International Search Report and Written opinion from PCT/EP2018/061445 dated Aug. 16, 2018.
International Search Report and Written Opinion from PCT/EP2018/061446 dated Aug. 16, 2018.
International Search Report and Written Opinion from PCT/EP2019/061444 dated Aug. 16, 2018.

* cited by examiner

PULSE SPECTROSCOPY

RELATED APPLICATIONS

The present application claims the benefit under 35 U.S.C. § 119(e) of U.S. Provisional Application Ser. No. 62/501,522, entitled "Improved SNR of Components in PPG Signal," filed May 4, 2017, Provisional Application Ser. No. 62/571,606, entitled "Improved Optical Cardiac Monitor," filed Oct. 12, 2017, Provisional Application Ser. No. 62/580,308, entitled "Improved Optical Cardiac Monitor," filed Nov. 1, 2017, and Provisional Application Ser. No. 62/580,024, entitled "User Body Hydration," filed Nov. 1, 2017. The above-referenced Provisional Applications are herein incorporated by reference in their entireties.

BACKGROUND

Pulse spectroscopy is the observation and analysis of optical signals that are directed at human skin in order to determine blood-related and cardiac physiological metrics and information such as a user's heart rate, pulse oximetry level (blood oxygen saturation), and hematocrit level, or a hematometry ratio. Pulse oximetry level, also known as "pulse ox" or SpO2, is a level of blood oxygen saturation. Red blood cells contain oxygenated hemoglobin (oxyhemoglobin, O2Hb) and deoxygenated hemoglobin (deoxyhemoglobin, HHb). A user's pulse oximetry increases as the concentration of oxygenated hemoglobin increases. Hematocrit level, also known as Hct, is the volume percentage (vol %) of red blood cells in blood and is commonly associated with a volume percentage of water in the blood.

Pulse spectroscopy may be performed by devices such as an electronic fitness device in contact with a wearer's skin. The user (wearer) may be any individual who wears the electronic device such that a housing of the electronic device is located proximate to skin of the individual (e.g., worn against the person's wrist, abdomen, leg, etc.). The electronic fitness device may include optical devices, such as an optical transmitter, which emits a plurality of optical signals (light), each having a unique wavelength, into the user's skin, and an optical receiver, which receives reflections of the optical signals (light) from the skin and generates a plurality of photoplethysmogram (PPG) signals, each including characteristics resulting from, or corresponding to, the wavelength of the received light. The PPG signals are analyzed to determine the blood-related and cardiac information.

While some conventional electronic devices utilize a reflection of optical signals emitted into a user's skin to determine the cardiac monitoring information, other electronic devices may emit a transmissive optical signal that passes through the user's skin (e.g., through a fingertip of a user). The conventional devices may include a plurality of housings such that a first housing includes an optical transmitter that emits an optical signal into the user's skin, such as the skin of a fingertip, and a second housing includes an optical receiver that receives the optical signal that are passed through the user's skin. Such electronic devices may be used in a location on a user's body where light can be transmitted without excessive attenuation through the tissue without depending on reflection from tissue, such as through a fingertip or an earlobe.

SUMMARY

Embodiments of the present technology provide an electronic fitness device for performing pulse spectroscopy. An embodiment of the electronic fitness device broadly comprises a housing, a first optical transmitter, an optical receiver, and a processing element. The housing includes a bottom wall. The first optical transmitter is positioned along the bottom wall and is configured to transmit a first optical signal and a second optical signal. The optical receiver is positioned along the bottom wall and is configured to receive the first and second optical signals modulated by the skin of the user and to generate first and second photoplethysmogram (PPG) signals resulting from the received optical signals. The processing element is in electronic communication with the first optical transmitter and the optical receiver. The processing element is configured to control the first optical transmitter to transmit the first optical signal during a first period of time and the second optical signal during a second period of time, receive the first and second PPG signals from the optical receiver, compare the first and second PPG signals, identify a common component present in the first and the second PPG signals based on the comparison, determine a signal filter parameter based on the common component, generate a first cardiac component from the first PPG signal based on the signal filter parameter, generate a second cardiac component from the second PPG signal based on the signal filter parameter, and determine blood-related physiological information based on the first and second cardiac component.

Another embodiment of the present technology provides an electronic fitness device broadly comprising a housing, a first optical transmitter, a second optical transmitter, a first optical receiver, and a processing element. The housing includes a bottom wall. The first optical transmitter is positioned along the bottom wall and is configured to transmit a first optical signal having a first wavelength. The second optical transmitter is positioned along the bottom wall and is configured to transmit a second optical signal having a second wavelength. The first optical receiver is positioned along the bottom wall and is configured to receive the first and second optical signals modulated by the skin of the user and to generate first and second photoplethysmogram (PPG) signals resulting from the received optical signals. The processing element is in electronic communication with the first optical transmitter, the second optical transmitter, and the first optical receiver. The processing element is configured to control the first optical transmitter to transmit the first optical signal during a first period of time and the second optical transmitter to transmit the second optical signal during a second period of time, respectively, receive the first and second PPG signals from the optical receiver, compare the first and second PPG signals, identify a common component present in the first and the second PPG signals based on the comparison, determine a signal filter parameter based on the common component, generate a first cardiac component from the first PPG signal based on the signal filter parameter, generate a second cardiac component from the second PPG signal based on the signal filter parameter, and determine blood-related physiological information based on the first and second cardiac component.

Yet another embodiment of the present technology provides an electronic fitness device broadly comprising a housing, a first optical transmitter, a second optical transmitter, an optical receiver, and a processing element. The housing includes a bottom wall. The first optical transmitter is positioned along the bottom wall and is configured to transmit a first optical signal having a first wavelength. The second optical transmitter is positioned along the bottom wall and is configured to transmit a second optical signal having a second wavelength. The optical receiver is positioned along the bottom wall and is configured to receive first and second optical signals modulated by the skin of the user and to generate a photoplethysmogram (PPG) signal resulting from the received optical signals. The processing element is in electronic communication with the first and second optical transmitters and the optical receiver. The processing element is configured to control the first and second optical transmitters to transmit the first optical signal and the second optical signal, respectively, receive a reference PPG signal from the optical receiver resulting from the first optical signal, receive a second PPG signal from the optical receiver resulting from the second optical signal, determine a signal characteristic of the reference PPG signal, process the second PPG signal utilizing the determined signal characteristic to generate a cardiac component of the second PPG signal, and determine blood-related physiological information based on the first cardiac component.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present technology will be apparent from the following detailed description of the embodiments and the accompanying drawing figures.

BRIEF DESCRIPTION OF THE DRAWING FIGURES

Embodiments of the present technology are described in detail below with reference to the attached drawing figures, wherein.

Figure 12:
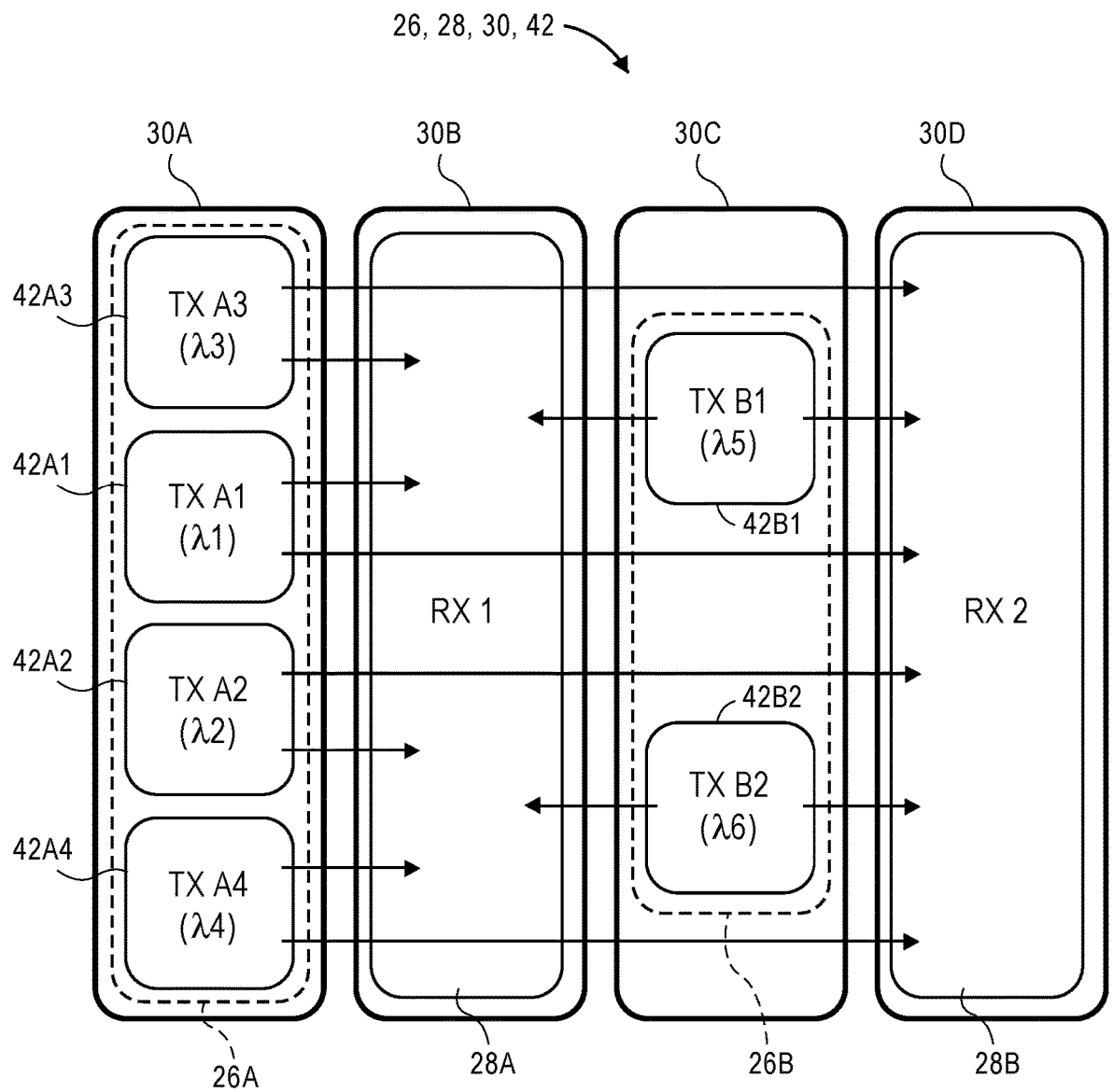
Figure 13:
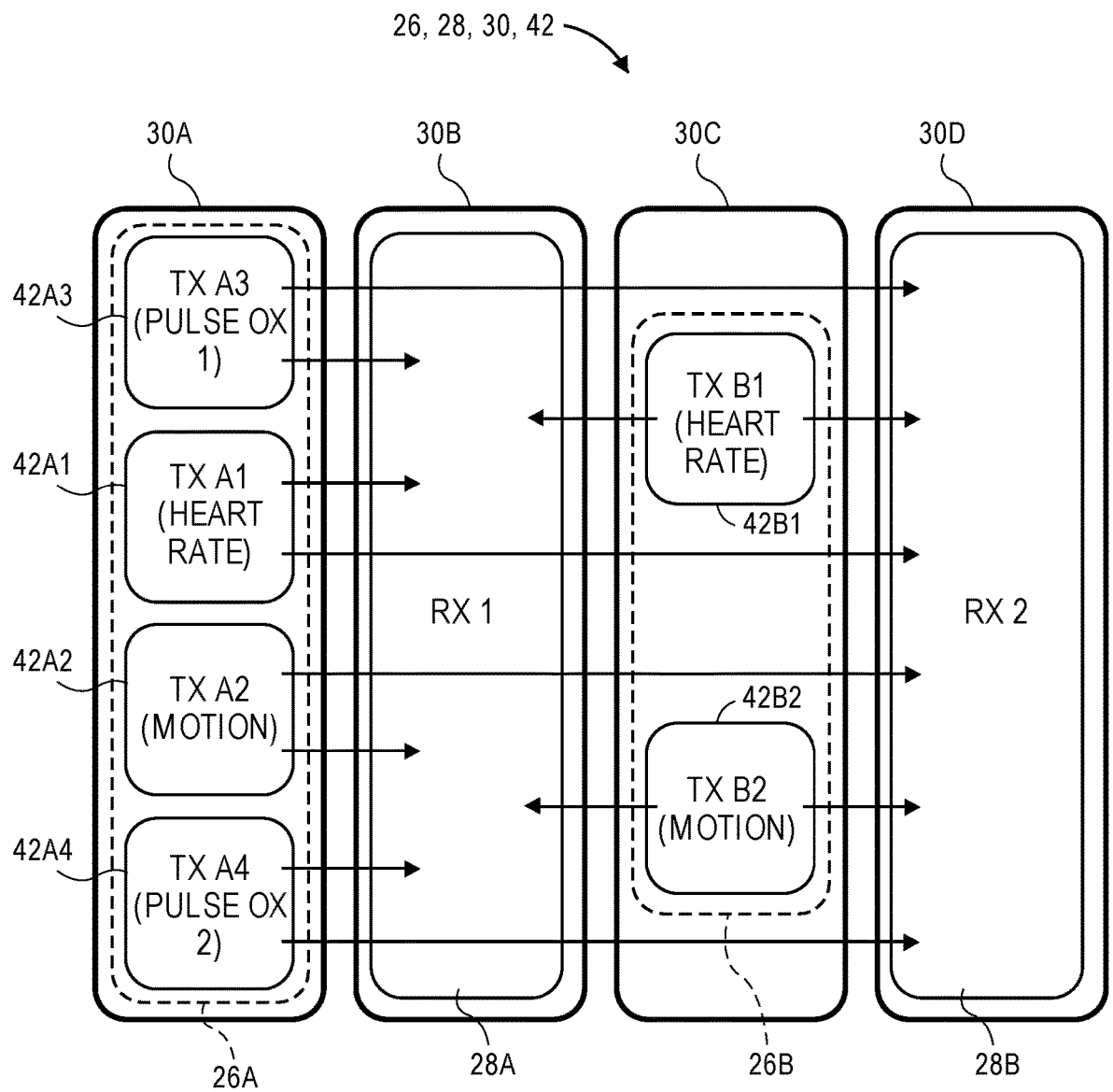
Figure 14:
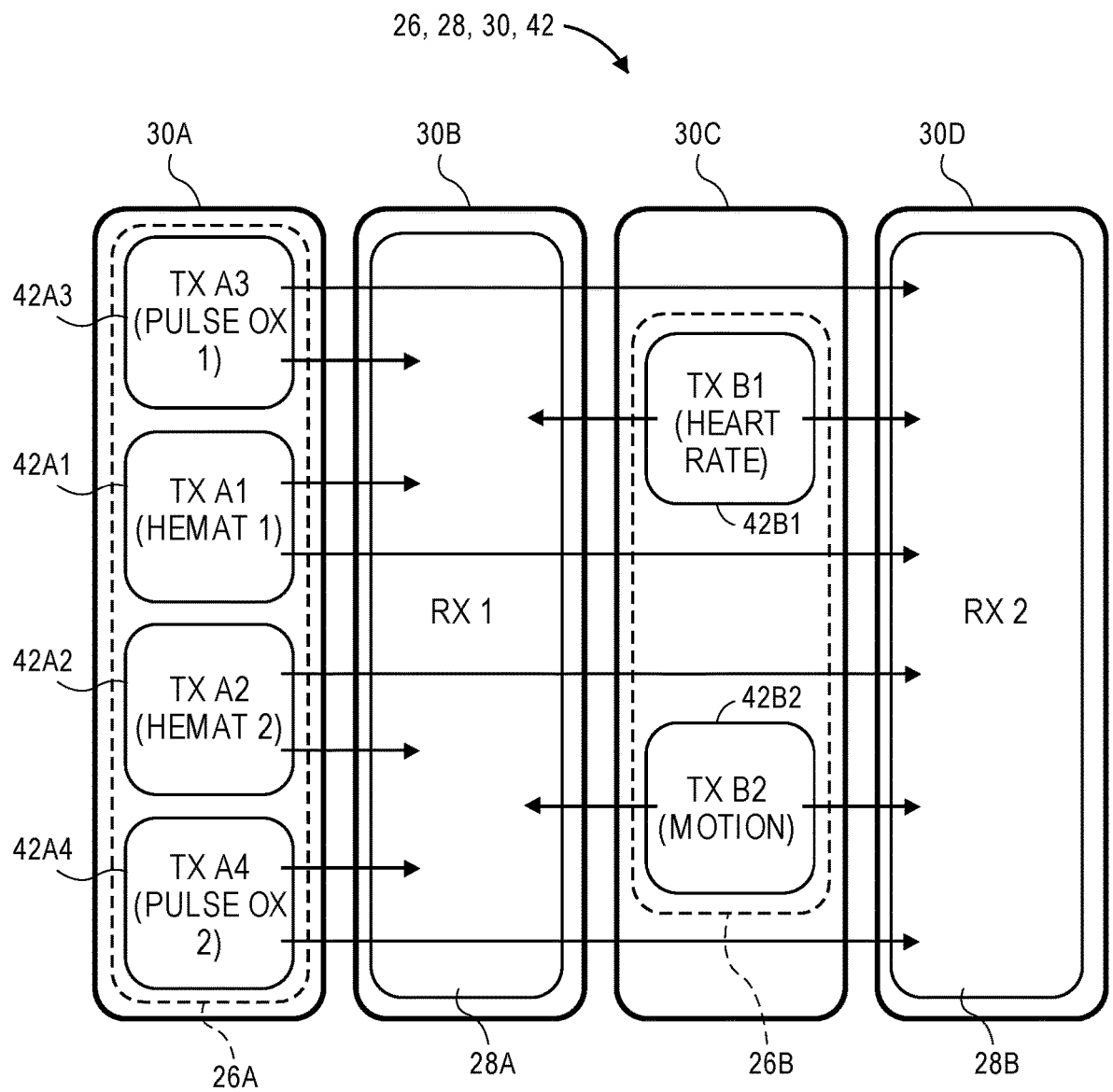
Figure 15:
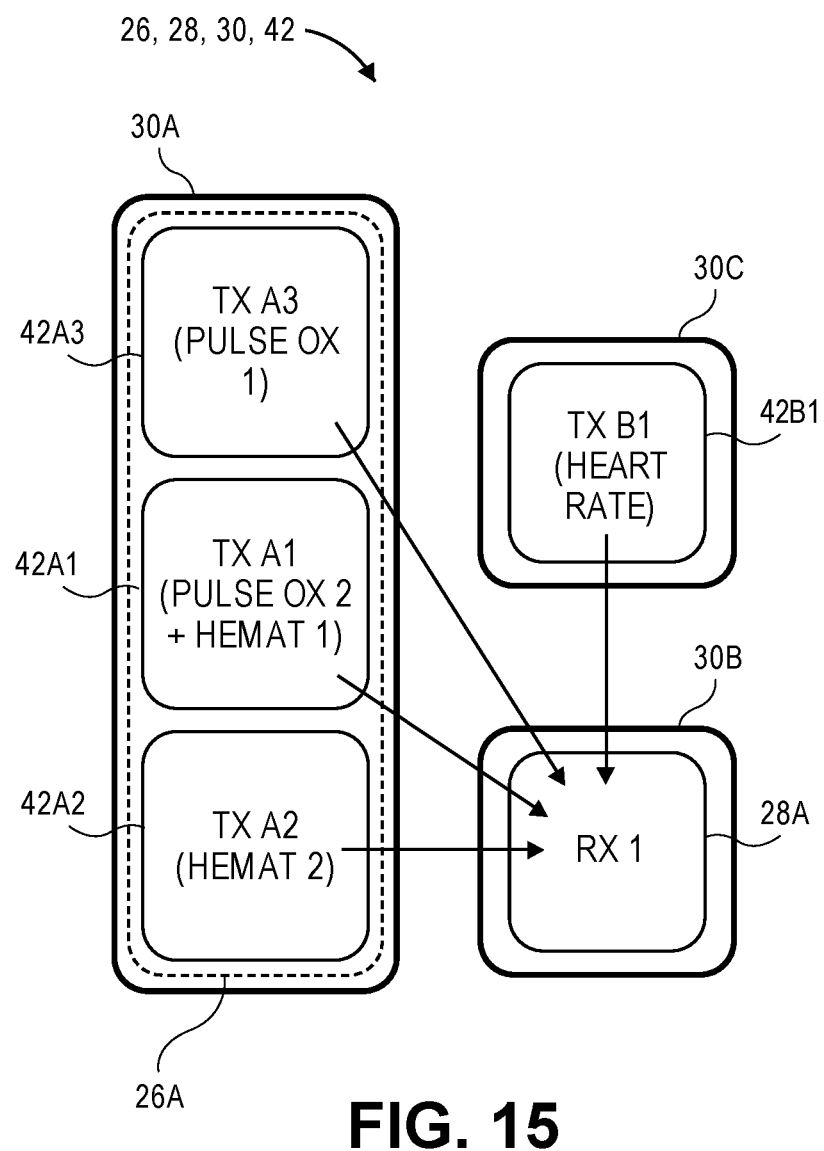

FIG. 12 is a schematic view of a plurality of optical transmitter arrays and optical receivers illustrating pathways of the optical signal transmitted by each of the optical transmitters and received by a plurality of optical receivers; and FIGS. 13-15 are other schematics of the optical transmitters and optical receivers of FIG. 12, the optical transmitters configured to output optical signals utilized to implement the indicated functions based on the optical signals received by the optical receivers.

The drawing figures do not limit the present technology to the specific embodiments disclosed and described herein. While the drawings do not necessarily provide exact dimensions or tolerances for the illustrated components or structures, the drawings are to scale as examples of certain embodiments with respect to the relationships between the components of the structures illustrated in the drawings.

DETAILED DESCRIPTION

The following detailed description of the technology references the accompanying drawings that illustrate specific embodiments in which the technology can be practiced. The embodiments are intended to describe aspects of the technology in sufficient detail to enable those skilled in the art to practice the technology. Other embodiments can be utilized and changes can be made without departing from the scope of the present technology. The following detailed description is, therefore, not to be taken in a limiting sense. The scope of the present technology is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Spectroscopic methods and techniques may be utilized to analyze characteristics a variety of materials and substances based on an interaction of electromagnetic radiation (light) with the materials and substances. For example, spectroscopy may be applied to the absorption, emission, and scattering of visible, infrared (IR), ultraviolet (UV), X-ray, microwave, and radio wave electromagnetic radiation with various materials and substances. Optical spectroscopy techniques may be applied using optical materials to disperse and/or focus visible, IR and UV light with materials and substances, such as the skin or tissue of a user. The electromagnetic radiation (light) oscillates as it travels and a wavelength of the oscillating electromagnetic radiation may be within a band associated with one of the visible, infrared (IR), and ultraviolet (UV) spectrum. The properties of certain materials and substances may influence the electromagnetic radiation as it passes through those materials and substances. As a result, the impact of particular materials and substances on electromagnetic radiation of certain wavelengths is generally known or otherwise measurable.

Conventional spectroscopy methods and techniques may include correlated spectroscopy, which includes analysis by comparing correlated signals, as well as augmented spectroscopy, which includes applying information determined from a reference signal to analyze another signal. Optical spectroscopy techniques applied to determine pulsatile blood-related and cardiac physiological metrics and information of a user may be referred to as optical "pulse" spectroscopy.

Figure 5A:
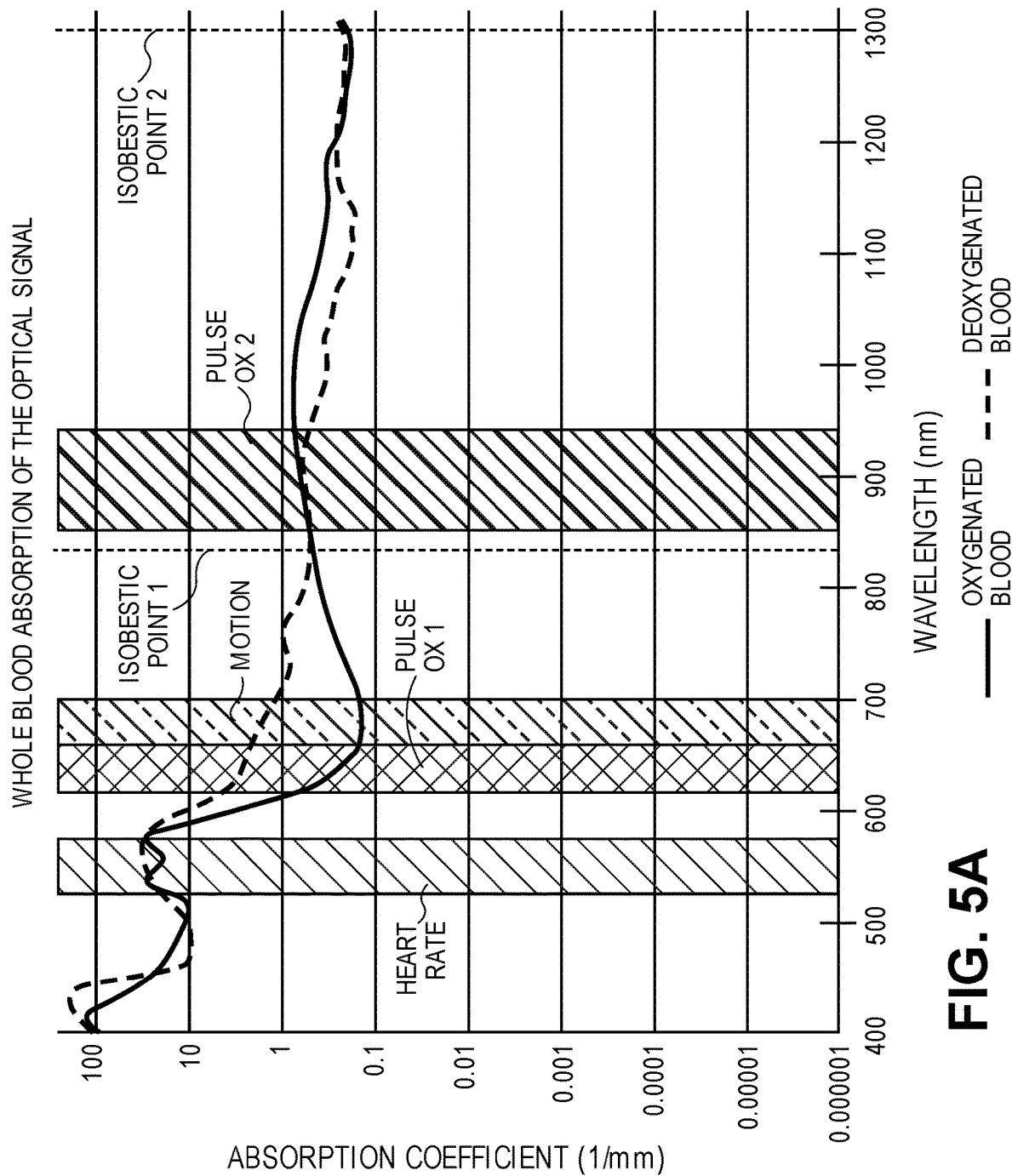
FIG. 5A is a plot of an absorption coefficient, or level, of the optical signal versus a wavelength of the optical signal, wherein the optical signal may be absorbed by various components of blood, such as oxygenated blood and deoxygenated blood.
Figure 5B:
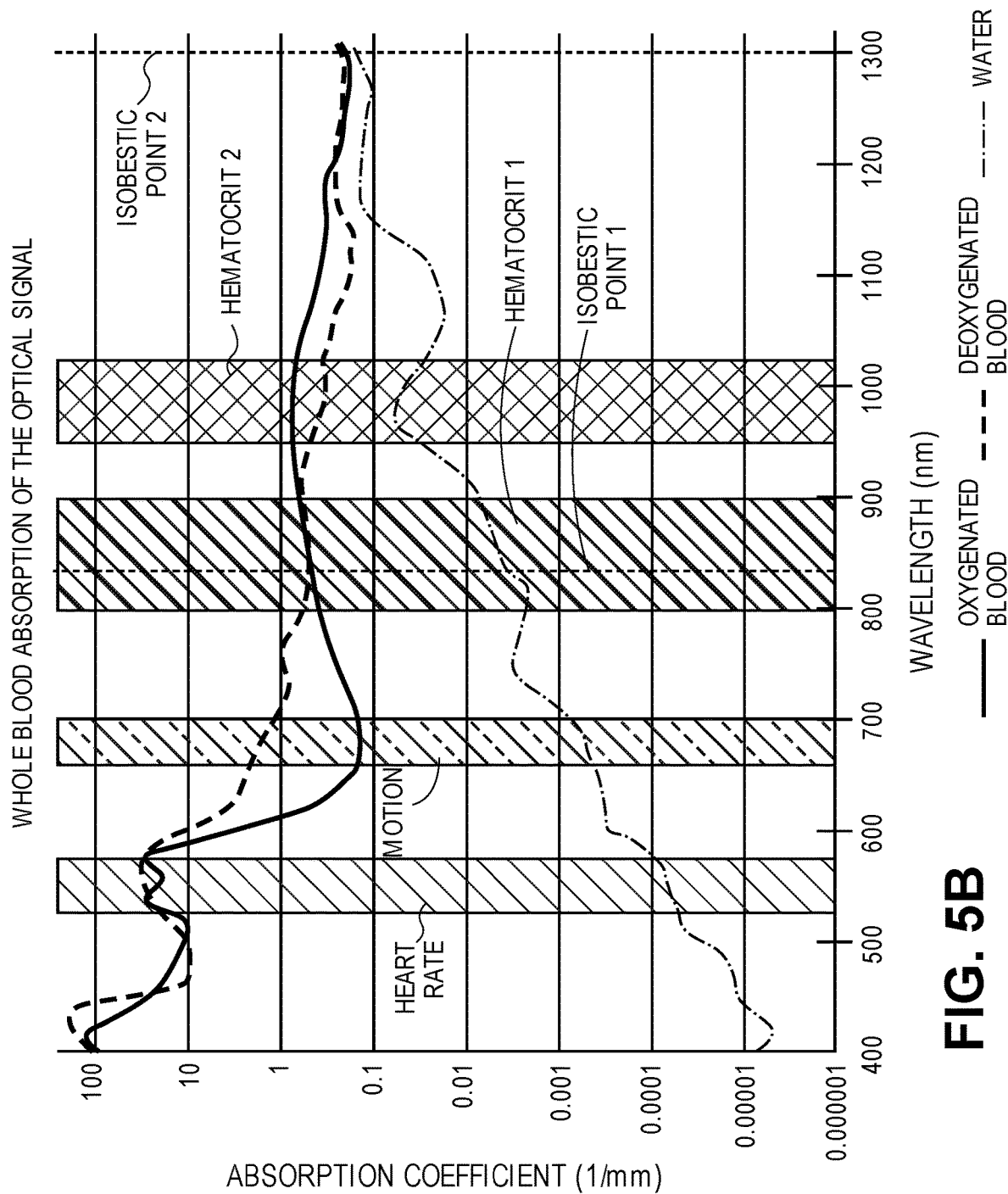
FIG. 5B is a plot of an absorption coefficient, or level, of the optical signal versus a wavelength of the optical signal, wherein the optical signal may be absorbed by various components of blood, such as oxygenated blood, deoxygenated blood, and water.

As shown in FIGS. 5A-5B, plots of an absorption level of an optical signal versus a wavelength of the optical signal are provided for oxygenated blood, deoxygenated blood, and water. Optical "pulse" spectroscopy techniques applied to determine blood-related and cardiac physiological metrics and information, such as a user's heart rate, a pulse oximetry level, a hematocrit level, and the like, may utilize one or more optical signals having wavelengths that are selected based on a relationship between the absorption level of an optical signal in oxygenated blood, deoxygenated blood, water, or any combination thereof. For example, some conventional optical spectroscopy techniques utilize the absorption level for oxygenated blood and deoxygenated blood to determine blood-related and cardiac physiological metrics and information by emitting one or more optical signals having a wavelength corresponding to points within the plot of FIG. 5A at which the absorption level of the oxygenated and deoxygenated blood is high (e.g., the band labeled "heart rate"), the least variance or separation (e.g., an intersection point at which the absorption level of the oxygenated and deoxygenated blood is substantially equal, such as the points labeled "isobestic point 1" and "isobestic point 2"), or any other wavelength at which the absorption level of the oxygenated and deoxygenated blood is measurable.

Figure 1:
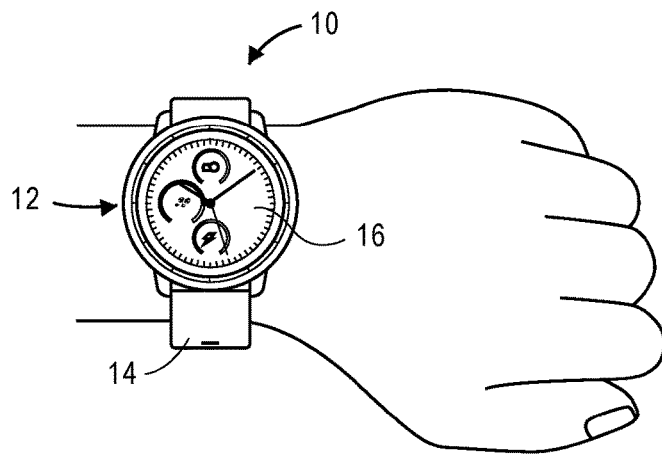
FIG. 1 is a top view of an electronic fitness device, constructed in accordance with various embodiments of the present technology, worn on a user's wrist.
Figure 2:
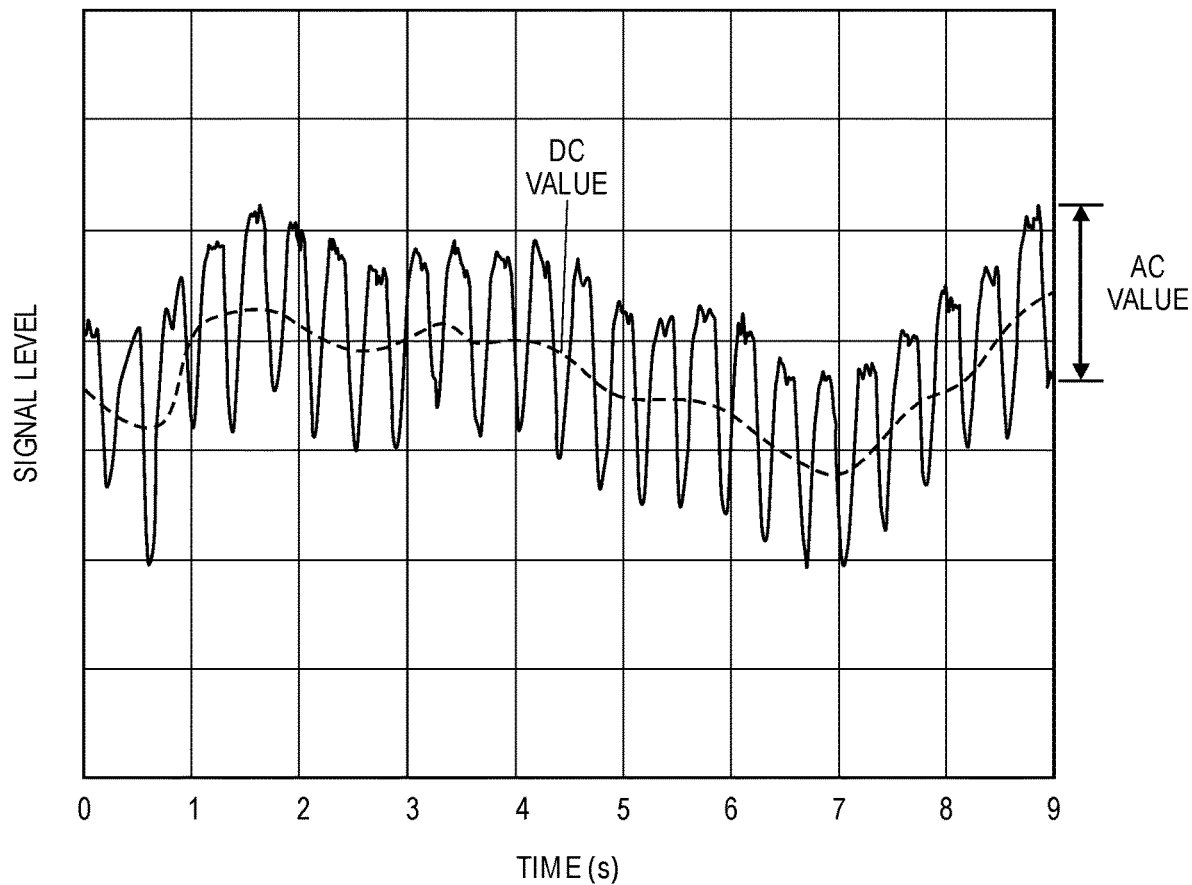
FIG. 2 is a plot of a photoplethysmogram (PPG) signal waveform that may be generated by the electronic fitness device over a period of time.

Embodiments of the present technology provide an electronic fitness device that may be worn on a user's wrist, such as the electronic fitness device shown in FIG. 1, and non-invasively determines blood-related and cardiac physiological metrics and information by analyzing one or more photoplethysmogram (PPG) signals, such as the PPG signal shown as a waveform in FIG. 2, using pulse spectroscopy techniques. The metrics and information may include the user's pulse or heart rate, a pulse oximetry ("Pulse Ox") level (also known as SpO2), a hematocrit level (also known as Hct), an estimated stress level, a maximum rate of oxygen consumption (VO2 max), or the like.

The electronic fitness device may determine a pulse oximetry level (blood oxygen saturation) and pulse oximetry indicator for the user and utilize a relationship stored in memory associating the determined pulse oximetry level and pulse oximetry indicator for the user. A processing element of the electronic fitness device may use two PPG signals to determine an indicator, which is equal to a first quotient of the AC value and the DC value at a first optical signal wavelength divided by a second quotient of the AC value and the DC value at a second optical signal wavelength. The processing element, electronically coupled to a memory element of the electronic fitness device, may determine the user's pulse oximetry, or percentage of oxygen in the blood, based on the pulse oximetry indicator (EQ. 1) and a relationship stored in a memory element that associates the pulse oximetry indicator and a value of the user's pulse oximetry. The indicator may be given by equation EQ. 1, wherein $\lambda 1$ is the first optical signal wavelength, and $\lambda 2$ is the second optical signal wavelength:

$$\text{Pulse Oximetry Indicator} = \frac{AC_{\lambda 1}/DC_{\lambda 1}}{AC_{\lambda 2}/DC_{\lambda 2}} \quad [\text{EQ. 1}]$$

The electronic fitness device may determine a hematometry ratio ("R") by analyzing two PPG signals and may further determine a hematocrit level (a concentration of red blood cells in blood). The electronic fitness device may also determine a total hemoglobin for user based on the hematometry ratio or the hematocrit level. In embodiments, the electronic device may utilize a relationship stored in memory associating the determined hematocrit level and/or hematometry ratio with a hydration level of the user or an anemic level of the user. A processing element of the electronic fitness device may use two PPG signals to determine a hematometry ratio "R" (EQ. 2) for the optical signal wavelengths and a hematocrit level using the following relationship (EQ. 3), in which $k_A$, $k_B$, $k_C$, $k_D$ are empirical or calculated constants calibrated for each system, and wherein $\lambda 1$ is the first optical signal wavelength and $\lambda 2$ is the second optical signal wavelength:

$$\text{Hematometry Ratio } (R) = \frac{AC_{\lambda 1}/DC_{\lambda 1}}{AC_{\lambda 2}/DC_{\lambda 2}} \quad [\text{EQ. 2}]$$

$$\text{Hematocrit Level} = [k_A + (k_B)(R)]/[k_C + (k_D)(R)] \quad [\text{EQ. 3}]$$

It is to be understood that the first and second optical signal wavelengths ($\lambda 1$, $\lambda 2$) for the pulse oximetry indicator (EQ. 1) are independent of the first and second optical signal wavelengths ($\lambda 1$, $\lambda 2$) for the hematometry ratio "R" (EQ. 2). As shown in FIG. 5A, the first and second optical signal wavelengths ($\lambda 1$, $\lambda 2$) for the pulse oximetry indicator (EQ. 1) may be selected from within the "pulse ox 1" band and the "pulse ox 2" band, respectively. Similarly, as shown in FIG. 5B, the first and second optical signal wavelengths ($\lambda 1$, $\lambda 2$) for the hematometry ratio "R" (EQ. 2) may be selected from within the "hematocrit 1" band and the "hematocrit 2" band, respectively, or substantially equal to "isobestic point 1" and "isobestic point 2." In some embodiments, as detailed below, a wavelength may be common to the pulse oximetry indicator (EQ. 1) and the hematometry ratio "R" (EQ. 2). For example, because the "pulse ox 2" band and the "hematocrit 1" band overlap from 850 nm to 900 nm, any wavelength between 850 nm and 900 nm may be selected for use as both the second optical signal wavelength ($\lambda 2$) for the pulse oximetry indicator (EQ. 1) and the first optical signal wavelength ($\lambda 1$) for the hematometry ratio "R" (EQ. 2).

In embodiments, the electronic fitness device may determine blood content of one or more dyshemoglobin: carboxyhemoglobin (COHb), methemoglobin (MHb), sulfhemoglobin (SHb) in addition to determining oxyhemoglobin (O2Hb), deoxyhemoglobin (HHb) and hematocrit (Hct). In an embodiment determining HHb, O2Hb, COHb and Hct content, at least four PPG signals with different optical signal wavelengths $\lambda 1$, $\lambda 2$, $\lambda 3$, $\lambda 4$ are used to determine HHb content ($V_{HHb}$), O2Hb content ($V_{O2Hb}$), COHb content ($V_{COHb}$) and plasma content ($V_P$). A ratio of AC to DC ($ACR_{\lambda,n}$) is determined for each wavelength n=1, 2, 3, 4 (EQ. 4). Subsequently, a simultaneous set of linear equations (EQ. 5-8) is solved for content of each component, where $c_n$, $k_{An}$, $k_{Bn}$, $k_{Cn}$, $k_{Dn}$ are empirical or calculated constants. Subsequently, determined values of $V_{HHb}$, $V_{O2Hb}$, $V_{COHb}$ and $V_P$, are used to determine a blood oxygen saturation (SpO2, EQ. 9), carboxyhemoglobin saturation (SpCO, EQ. 10) and hematocrit (EQ. 11). In an embodiment, an additional PPG signal with optical signal wavelength $\lambda_5$ is used to as a cardiac signal reference. In an embodiment, referring to FIGS. 5A-fB, $\lambda_1$ is in the "pulse ox 1" band, $\lambda_2$ is in the "hematocrit 1" band, $\lambda_3$ is in the "hematocrit 2" band, $\lambda_4$ is in the 700-760 nm band and $\lambda_5$ is in the "heart rate" band.

$$ACR_{\lambda,n} = AC_{\lambda,n}/DC_{\lambda,n} + c_n [n=1,2,3,4] \quad [\text{EQ. 4}]$$

$$ACR_{\lambda,1} = V_P k_{A1} + V_{HHb} k_{B1} + V_{\lambda,O2Hb} k_{C1} + V_{COHb} k_{D1} \quad [\text{EQ. 5}]$$

$$ACR_{\lambda,2} = V_P k_{A2} + V_{HHb} k_{B2} + V_{O2Hb} k_{C2} + V_{COHb} k_{D2} \quad [\text{EQ. 6}]$$

$$ACR_{\lambda,3} = V_P k_{A3} + V_{HHb} k_{B3} + V_{O2Hb} k_{C3} + V_{COHb} k_{D3} \quad [\text{EQ. 7}]$$

$$ACR_{\lambda,4} = V_P k_{A4} + V_{HHb} k_{B4} + V_{O2Hb} k_{C4} + V_{COHb} k_{D4} \quad [\text{EQ. 8}]$$

$$SpO2 = V_{O2Hb}/(V_{HHb} + V_{O2Hb} + V_{COHb}) \quad [\text{EQ. 9}]$$

$$SpCO = V_{COHb}/(V_{HHb} + V_{O2Hb} + V_{COHb}) \quad [\text{EQ. 10}]$$

$$Hct = (V_{HHb} + V_{O2Hb} + V_{COHb})/(V_P + V_{HHb} + V_{O2Hb} + V_{COHb}) \quad [\text{EQ. 11}]$$

In embodiments, the electronic fitness device may utilize correlated pulse spectroscopy techniques, augmented pulse spectroscopy techniques, or any combination thereof, to determine blood-related and cardiac physiological metrics and information of a user. For instance, as shown in FIGS. 5A-5B, embodiments of the disclosed electronic fitness device may utilize either PPG signal to determine a user's heart rate (pulse) by controlling one or more optical transmitters to emit one or more optical signals (light) having a wavelength within the band labeled "heart rate." Similarly, embodiments of the disclosed electronic fitness device may utilize correlated or augmented pulse spectroscopy techniques to determine a pulse oximetry level for the user by controlling one or more optical transmitters to emit one or more optical signals having a wavelength within the band(s) labeled "pulse ox 1" (630 nm-670 nm) and/or "pulse ox 2" (850 nm-950 nm) within the plot of FIG. 5A. Additionally, in embodiments, the electronic fitness device may utilize correlated or augmented pulse spectroscopy techniques to determine a hematocrit level by controlling one or more optical transmitters to emit optical signals (light) having a wavelength corresponding to a wavelength at which the absorption level of the oxygenated and deoxygenated blood is substantially equal, such as "isobestic point 1" or "isobestic point 2" (thereby reducing any impact resulting from oxygenation differences in a user's blood). In other embodiments, the electronic fitness device may utilize correlated or augmented pulse spectroscopy techniques to determine a hematocrit level by controlling one or more optical transmitters to emit optical signals (light) having a wavelength within the bands labeled "hematocrit 1" (800 nm-900 nm) and/or "hematocrit 2" (950 nm-1025 nm) within the plot of FIG. 5B.

Figure 3:
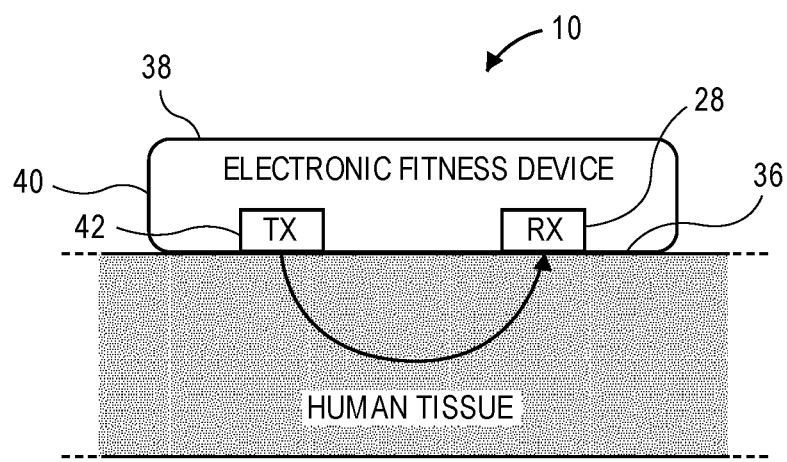
FIG. 3 is a schematic side sectional view of the electronic fitness device and a user's wrist depicting transmission of an optical signal through the skin and tissue of the user.
Figure 4:
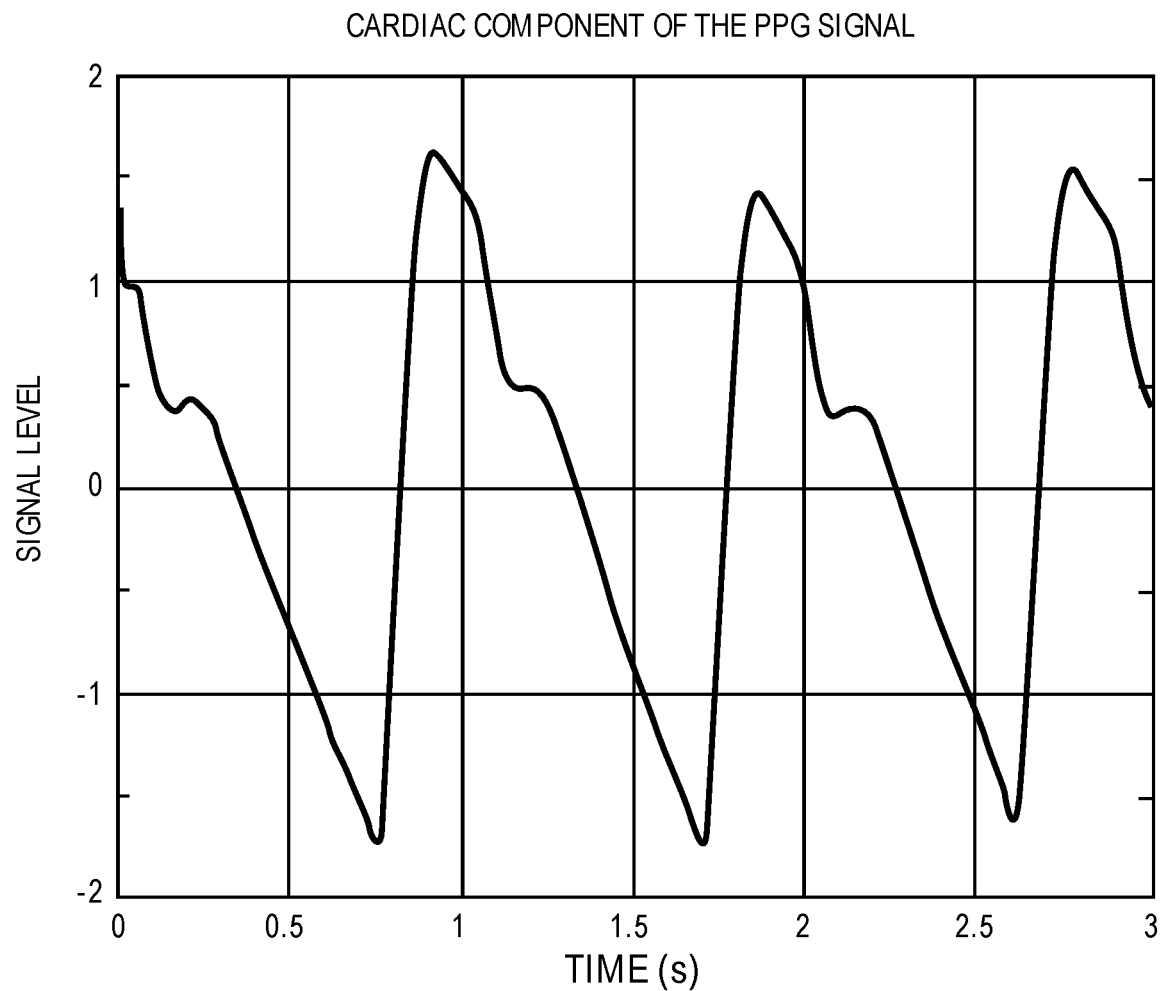
FIG. 4 is a plot of a cardiac component of the PPG signal resulting from the PPG signal being filtered.

Referring to FIG. 3, a PPG signal is based on an optical signal (light) emitted from an optical transmitter (TX) into the user's skin (human tissue) proximate to the optical transmitter (TX). The user (wearer) may be any individual who wears the electronic device such that a housing of the electronic device is located proximate to skin of the individual (e.g., worn against the person's wrist, abdomen, leg, etc.). The emitted optical signal penetrates the user's skin with substantial energy to a depth that ranging from tens of microns to several millimeters depending on a variety of criteria, such as the wavelength of transmitted light, presence of blood vessels and composition of the user's skin layers. A portion of the optical signal is reflected, or otherwise transferred, from the skin to an optical receiver (RX), typically a photodiode, that generates the PPG signal. The magnitude of the PPG signal is associated with an intensity of the received optical signal (light). The optical signal may be modulated, or otherwise modified, by the flow of blood through the vessels in the path of the optical signal. Specifically, the optical signal is modulated by the blood flow response to the beating of the user's heart, or the cardiac cycle. Thus, the optical signal received by the optical receiver (RX) has been modulated to include a cardiac component corresponding to the user's cardiac characteristics, which are associated with the user's heartbeat. In turn, the PPG signal generated by the optical receiver (RX) includes a cardiac component corresponding to the effect of the user's heartbeat on the flow of blood in the vessels. In addition to the cardiac component, the PPG signal includes undesirable components, such as a motion component resulting from motion of the user, noise components resulting from operation of the device and/or electronic circuitry of the optical receiver (RX), etc. An example of the cardiac component of the PPG signal, in isolation with other components removed or filtered, is shown in FIG. 4.

Generally, as seen in FIG. 2, the PPG signal waveform includes an AC component and a DC component. The AC component of the PPG signal waveform oscillates between a local maximum and a local minimum over successive short periods of time. The DC component of the PPG signal waveform may be a moving average of the local maximum and the local minimum over successive short periods of time. In some implementations, a processing element may control a low-pass filter to remove the DC component or a substantial portion of the DC component. A source of low-frequency AC noise, such as a motion component, may be included in the DC value, causing the PPG signal waveform to move up or down. Some low-frequency AC noise components, having frequencies similar to the cardiac component, modulate the envelope of and/or otherwise distort the cardiac component of the PPG signal. Noise inherent in the transmission of the optical signals through a user's skin or tissue as well as motion and other AC noise components may make the identification and extraction of the cardiac component, such as the one shown in FIG. 4, by the processing element difficult.

FIGS. 5A-5B are plots that show an absorption coefficient, or level of absorption, of various components of blood, including oxygenated blood, deoxygenated blood, and water, for an optical signal emitted by an optical transmitter having one of the plurality of wavelengths ranging from 400 nanometers (nm) to 1300 nm. As shown in FIGS. 5A-5B, the absorption of the optical signal is different across the spectrum of 400-1300 nm for each blood component, such as oxygenated blood, deoxygenated blood or water. As a result, transmitting and receiving an optical signal having one of the illustrated wavelengths may enable a processing element to determine information about a user's blood and cardiac condition based on known absorption characteristics of the blood at that wavelength. In embodiments, the processing element may control a plurality of optical transmitters (independent or part of an optical transmitter array) to transmit a plurality of optical signals each having a single wavelength and the processing element may control one or more optical receivers to generate a PPG signal based on reflections of the optical signals received from the user's skin or tissue.

As shown in FIG. 5A, a processing element may control an optical transmitter to emit an optical signal having a wavelength that is within one of a plurality of ranges (bands) of wavelengths labeled for use, such as heart rate and pulse oximetry, and use a PPG signal generated based on reflections of the optical signal received from the user's skin or tissue for the corresponding use. For example, in embodiments, an optical transmitter may be controlled to emit an optical signal having a wavelength of 550 nm (green light), which is within a band labeled "heart rate," and the processing element may utilize a PPG signal generated by an optical receiver based on received reflections of the optical signal to determine a user's heart rate. Similarly, the processing element may control a first optical transmitter to emit a first optical signal having a wavelength of 650 nm (red light), which is within a band labeled "pulse ox 1," and/or a second optical transmitter to emit a second optical signal having a wavelength of 900 nm (infrared light that is not visible), which is within a band labeled "pulse ox 2," and utilize PPG signals generated by one or more optical receivers based on received reflections of the 650 nm and 900 nm optical signals to determine a user's pulse oximetry level.

As shown in FIG. 5B, a processing element may control an optical transmitter to emit an optical signal having a wavelength that is within one of a plurality of ranges (bands) of wavelengths labeled for use, such as heart rate and hematocrit level, and use a PPG signal generated based on reflections of the optical signal received from the user's skin or tissue for the corresponding use. For example, in embodiments, the processing element may control a first optical transmitter to emit a first optical signal having a wavelength of 550 nm (green light), which is within a band labeled "heart rate," a second optical transmitter to emit a second optical signal having a wavelength at a first isobestic point (830 nm), and a third optical transmitter to emit a third optical signal having a wavelength at a second isobestic point (1300 nm). The processing element may use PPG signals resulting from optical signal having a wavelength at the isobestic points, which correspond to wavelengths at which the absorption of the optical signal by oxygenated blood and deoxygenated blood is roughly the same, to determine information about the user's blood and/or heart without having account for any impact resulting from a level of oxygen in the user's blood.

In other embodiments, as shown in FIG. 5B, the processing element may control a first optical transmitter to emit a first optical signal having a wavelength of 850 nm (infrared light that is not visible), which is within a band labeled "hematocrit 1," and/or a second optical transmitter to emit a second optical signal having a wavelength of 1000 nm (infrared light that is not visible), which is within a band labeled "hematocrit 2," and utilize PPG signals generated by one or more optical receivers based on received reflections of the 850 nm and 1000 nm (1 um) optical signals to determine a user's hematocrit level. In some configurations, use of optical transmitters emitting optical signals at non-isobestic wavelengths may result in a ratio "R" (EQ. 2) that is simultaneously dependent on a user's hematocrit level (Hct) and blood oxygen saturation level (SpO2). In embodiments, the processing element may determine a hematocrit (Hct) and a blood oxygen saturation level (SpO2) by controlling optical transmitters to output optical signals having at least one additional wavelength, a third wavelength, such that a processor may determine at least two relationships of hematometry ratios (EQ. 2). For example, the processing element may determine a first hematometry ratio (R12 for a first and a second wavelength), a second hematometry ratio (R23 for a second and a third wavelength), and apply the determined hematometry ratios to determine the hematocrit level (Hct) and/or the blood oxygen saturation level (SpO2) based on a system of equations utilizing the first and second hematometry ratios (R12 and R23). For example, ratio R12 may be used to determine blood oxygen saturation level and subsequently, ratio R23, together with the previously determined blood oxygen saturation level may be used to determine blood hematocrit level. In this configuration, in EQ. 3 above, parameters $k_A$, $k_B$, $k_C$, $k_D$ may each be a function of blood oxygen saturation.

In embodiments, the electronic fitness device may include optical transmitters that emit an optical signal having a wavelength that is within one of a plurality of ranges (bands) of wavelengths labeled for use with simultaneously determining a heart rate, a pulse oximetry level and hematocrit level.

The electronic fitness device may include a memory element storing one or more computer-executable instructions that, when executed by the processing element, utilize a PPG signal resulting from an optical signal for a use identified in FIGS. 5A-5B corresponding to a wavelength. For example, a first range of wavelengths of an optical signal, labeled "heart rate," may correspond to absorption levels of the optical signal for oxygenated blood and deoxygenated blood that the processing element may determine as adequate or suitable for determining a user's heart rate because the optical signal may result in a PPG signal generated by an optical receiver that has a high signal to noise ratio (SNR) and/or a high signal to motion noise ratio (SMNR). The processing element may subsequently isolate a cardiac component from this high-SNR PPG signal and determine an accurate heart rate or pulse for the user. Similarly, a second range of wavelengths of the optical signal, labeled "motion," may correspond to absorption levels of the optical signal for oxygenated blood and deoxygenated blood that the processing element may determine as adequate or suitable for identifying a motion component within the PPG signal. The processing element may subsequently isolate the motion component from the PPG signal or utilize the PPG signal to reduce or minimize the motion component from other PPG signals resulting from optical signals having other wavelengths.

As described above, the processing element may receive PPG signals resulting from optical signals having a wavelength within the "pulse ox 1" and "pulse ox 2" bands and utilize those PPG signals to determine the user's pulse oximetry. In embodiments, the processing element may receive a first PPG signal generated based on a received optical signal transmitted into the skin or tissue having a first wavelength in the "pulse ox 1" range and a second PPG signal is generated based on a received optical signal transmitted having a second wavelength in the "pulse ox 2" range. The processing element may use the two PPG signals to determine an indicator, which is equal to a first quotient of the AC value and the DC value at a first optical signal wavelength divided by a second quotient of the AC value and the DC value at a second optical signal wavelength. The indicator may be given by equation EQ. 1, wherein $\lambda 1$ is the first optical signal wavelength, and $\lambda 2$ is the second optical signal wavelength, provided above.

The processing element, electronically coupled to the memory element, may determine the user's pulse oximetry, or blood oxygen saturation, based on the pulse oximetry indicator (EQ. 1) and a relationship stored in a memory element that associates the pulse oximetry indicator and a value of the user's pulse oximetry. In embodiments, the relationship may be expressed as a lookup table stored in the memory element that includes a plurality of pulse oximetry indicators and their associated pulse oximetry values for one or more health and/or physiological characteristics. Health characteristics may include age, gender, weight, height, physical condition (e.g., in good health, pulmonary conditions, etc.), and fitness class (i.e., overall physical fitness level). Physiological characteristics may include, but are not limited to, a heartbeat, heart rate, heart-rate variability, speed, distance traveled, calculating calories burned, body temperature, blood pressure, stress intensity level, body energy level, and the like. In embodiments, the processing element may identify a pulse oximetry value based on a determined pulse oximetry indicator (EQ. 1), one or more health characteristics (e.g., age, gender, or weight) and one or more physiological characteristics (e.g., heart rate, blood pressure or heart-rate variability).

As with other calculations determined using signals, accurate determination of the user's heart rate and pulse oximetry value may benefit from reduction of noise components in the PPG signal. For instance, accurate determination of the user's pulse oximetry, particularly the pulse oximetry indicator, may benefit from reduction of noise components and the motion component to enable use of a PPG signal having the SNR and/or the SMNR that is maximized. In environments where noise components are present in the PPG signal, it is desirable to remove the noise components from the PPG signal in order to isolate the cardiac component. Isolating the cardiac component may lead to faster and more accurate determination of the user's heart rate or other cardiac-related metrics. Various forms of pulse spectroscopy, such as correlated pulse spectroscopy and augmented pulse spectroscopy, may be utilized to isolate the cardiac component.

As described above, the processing element may receive PPG signals resulting from optical signals having a wavelength within the "hematocrit 1" and "hematocrit 2" bands and utilize those PPG signals to determine a concentration of red blood cells in blood, an absolute or relative body hydration level of the user, or an anemic level of the user. Common hematocrit levels for humans may be approximately 45-50% and changes in hematocrit levels may be indicative of various health and wellness conditions. For example, the memory element may store a relationship correlating a change in the hematometry ratio (EQ. 2) and/or the hematocrit level (EQ. 3) with changes in body hydration based on one or more health characteristics (e.g., age, gender, or weight) and one or more physiological characteristics (e.g., heart rate, blood pressure or heart-rate variability) of a user. Similarly, the memory element may store a relationship correlating a change in the hematometry ratio (EQ. 2) and/or the hematocrit level (EQ. 3) with changes in an anemic level based on one or more health characteristics (e.g., age, gender, or weight) and one or more physiological characteristics (e.g., heart rate, blood pressure or heart-rate variability) of a user.

As provided in EQ. 2 and EQ. 3 above, a relationship stored in a memory element may associate the hematometry ratio and a value of the user's concentration of red blood cells in blood, an absolute or relative body hydration level, or an anemic level. Similar to determined pulse oximetry levels, the relationship may be expressed as a lookup table stored in the memory element that includes a plurality of hematometry ratios and their associated concentration of red blood cells in blood, an absolute or relative body hydration level, or an anemic level for one or more health and/or physiological characteristics. Health characteristics may include age, gender, weight, height, physical condition (e.g., in good health, pulmonary conditions, etc.), and fitness class (i.e., overall physical fitness level). The optical system may include or be coupled with a memory device associating a plurality of hydration levels with hematocrit levels or changes in hematocrit levels. The memory may include hydration level information based on a user's age, sex, physical condition (e.g., in good health, pulmonary conditions, etc.).

Correlated pulse spectroscopy involves the processing element comparing, or correlating, two PPG signals to determine signal filter parameters that are utilized to actively adjust the operating parameters of a plurality of signal filters. Each signal filter then filters (removes) undesired components from one of a plurality of PPG signals. The processing element may begin the correlated pulse spectroscopy process by controlling one or more optical transmitters to transmit at least two optical signals that are differentiated in some fashion.

In embodiments, a difference between the two optical signals may be emission from optical transmitter at different times (while having the same wavelength and traveling the same path from the optical transmitter to the optical receiver). For example, the electronic fitness device may include a first optical transmitter that emits a first optical signal at a first period of time and a second optical signal at a second period of time. Alternatively, the electronic fitness device may include a first optical transmitter that emits a first optical signal at a first period of time and the electronic fitness device may include a second optical transmitter that emits a second optical signal at a second period of time.

In other embodiments, a difference between the two optical signals may be the two optical signals having different wavelengths. For example, the electronic fitness device may include a first optical transmitter that emits a first optical signal having a first wavelength (e.g., 650 nm-red light) at a first period of time and the electronic fitness device may include a second optical transmitter that emits a second optical signal having a second wavelength (e.g., 900 nm-infrared light) at the first period of time or at a second period of time. The first optical signal may travel from a first optical transmitter to a first optical receiver and the second optical signal may travel from the second optical transmitter to a second optical receiver. In embodiments, when the second optical signal may be emitted at the second period of time, the first optical signal and the second optical signal may travel from the first optical transmitter and the second optical transmitter, respectively, to the first optical receiver. Even though the optical signals may have different wavelengths, the optical signals may each have a wavelength in the "heart rate" range and one or more optical receivers may provide PPG signals with a high SNR and/or SMNR. The processing element may receive the two resulting PPG signals and remove their DC components by implementing high-pass filtering or other operations, such as level shifting.

In other embodiments, a difference between the two optical signals may be the two optical signals traveling along different paths from an optical transmitter to an optical receiver. Signal path diversity, which relates to differences in the paths that two optical signals travel, may be achieved or created by use of a plurality of optical transmitters and/or optical receivers. For example, the electronic fitness device may include a first optical transmitter that emits a first optical signal at a first period of time and a second optical signal at a second period of time. The first optical signal may travel from the first optical transmitter to a first optical receiver and the second optical signal may travel from the first optical transmitter to a second optical receiver. Alternatively, the electronic fitness device may include a first optical transmitter that emits a first optical signal at a first period of time that is received by a first optical receiver and the electronic fitness device may include a second optical transmitter that emits a second optical signal at the first period of time that is received by a second optical receiver. Similarly, the electronic fitness device may include a first optical transmitter that emits a first optical signal at a first period of time that is received by a first optical receiver and the electronic fitness device may include a second optical transmitter that emits a second optical signal at a second period of time that is received by a second optical receiver.

In embodiments, the electronic fitness device may include a first optical transmitter that emits a first optical signal at a first period of time, a second optical transmitter that emits a second optical signal at a second period of time, and a first optical receiver that receives the first and second optical signals transmitted by the first and second optical transmitters. Alternatively, the electronic fitness device may include a first optical transmitter that emits a first optical signal at a first period of time, a second optical transmitter that emits a second optical signal at the first period of time, and a first optical receiver that receives the first and second optical signals transmitted by the first and second optical transmitters.

The processing element may implement correlated pulse spectroscopy techniques for the two PPG signals to determine signal filter parameters that are utilized to actively adjust the operating parameters of a plurality of signal filters. Referring to FIGS. 6-8, and FIG. 10, the two PPG signals, PPG 1 and PPG 2, are input to a processing element 34 which includes various components for signal processing and filtering. The PPG 1 and PPG 2 signals are received by an active filter 44 in which they are generally compared, or specifically correlated, with one another, producing a signal that includes the signal component(s) common to both signals, which is a cardiac component present in PPG 1 and PPG 2. Other components that are not common to both PPG signals, such as noise components, are effectively filtered out in the signal output by correlation unit 46. The cardiac component common to both PPG signals is then utilized by processing element 34 to determine one or more signal filter parameters to be utilized with the active filter 44 and stored in the memory element 32. For example, one signal filter parameter may be a representation of the common cardiac component, such as a complete period of a common cardiac component waveform represented in the time domain. Additionally, or alternatively, the common cardiac component may be represented in the frequency domain by the processing element 34 performing a time domain to frequency domain transformation, such as a discrete Fourier transform (DFT) or other transform. The common cardiac component may also or instead be represented by the processing element 34 through transforms such as a discrete wavelet transform or similar mathematical operations. In embodiments, the processing element 34 may determine as signal filter parameters one or more spectral parameters of the cardiac component, such as the fundamental frequency, harmonic frequencies, bandwidth, phase, and the like. In yet another embodiment, the signal filter parameter may be a transfer function that is developed using either the first PPG signal or the second PPG signal as an input function and the common cardiac component as an output function.

The operation and performance of signal filters 48 may be determined or controlled by the determined signal filter parameters. For example, each signal filter 48 may compare other PPG signals to the time domain waveform or the frequency domain model of the common cardiac component. Alternatively, each signal filter 48 may use the time domain waveform or the frequency domain model to filter the other PPG signals. The signal filter 48 may be a band-pass filter with a pass band frequency determined by the spectral parameters or the frequency domain transform. The signal filter 48 may perform the transfer function. At any rate, the signal filter parameters are utilized by each signal filter 48 to maintain and/or adjust the operating parameters, such as pass frequency ranges, bandwidths, etc., for each of the signal filters 48.

In embodiments, an optical signal may be generated at a wavelength at which absorption of the optical signal by the blood vessels in the skin or tissue is low. The resulting PPG signals generated by an optical receiver based on reflections of the optical signal, in turn, may have a low SNR and/or SMNR. In such embodiments, still referring to FIGS. 6-8, these PPG signals, one or more of PPG 3-PPG n are input to a signal filter 48 configured using a signal filter parameter determined based on correlated pulse spectroscopy techniques applied to PPG 1 and PPG 2. Subsequently, each of PPG 3-PPG n is processed by the signal filter 48 to isolate a cardiac component CC 1-CC n of each input PPG signal.

Unlike correlated pulse spectroscopy, augmented pulse spectroscopy techniques involve analyzing a first signal, such a PPG signal with a high SNR and/or SMNR, to determine one or more signal characteristics of the first signal, which may serve as a reference signal used to process other signals by identifying, isolating, or generating a desired component (e.g., the cardiac component) for each of the other signals based on the determined signal characteristics. The processing element may begin the augmented pulse spectroscopy process by controlling one or more optical transmitters to transmit a first optical signal typically having a wavelength associated with an acceptable SNR or SMNR for a PPG signal resulting from reflections of the first optical signal to serve as a reference PPG signal for other PPG signals having lower SNR or SMNR. For example, the first optical signal may have a wavelength within the "heart rate" range (band) of FIGS. 5A-5B, which may result in a first PPG signal having a higher SNR or SMNR than a second optical signal having a wavelength within the "pulse ox 1" or "pulse ox 2" bands. The processing element may analyze the first PPG signal to determine one or more signal characteristics of the first PPG signal and use the determined one or more signal characteristics to process the second PPG signal by identifying, isolating, or generating a desired cardiac component for the second PPG signal based on the determined signal characteristics of the first PPG signal.

Figure 9:
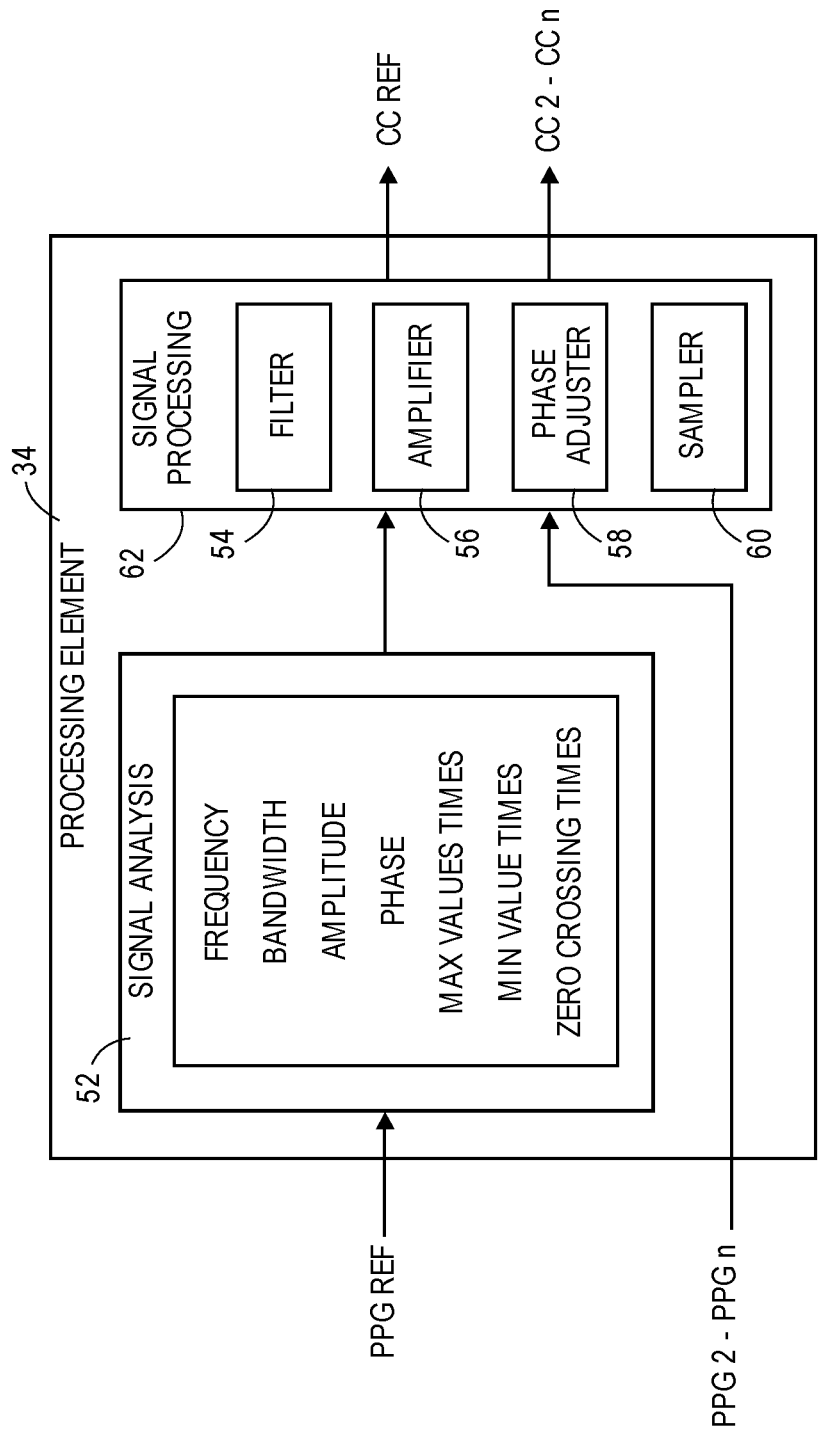
FIG. 9 is a schematic block diagram of one embodiment of a processing element for performing augmented pulse spectroscopy.
Figure 10:
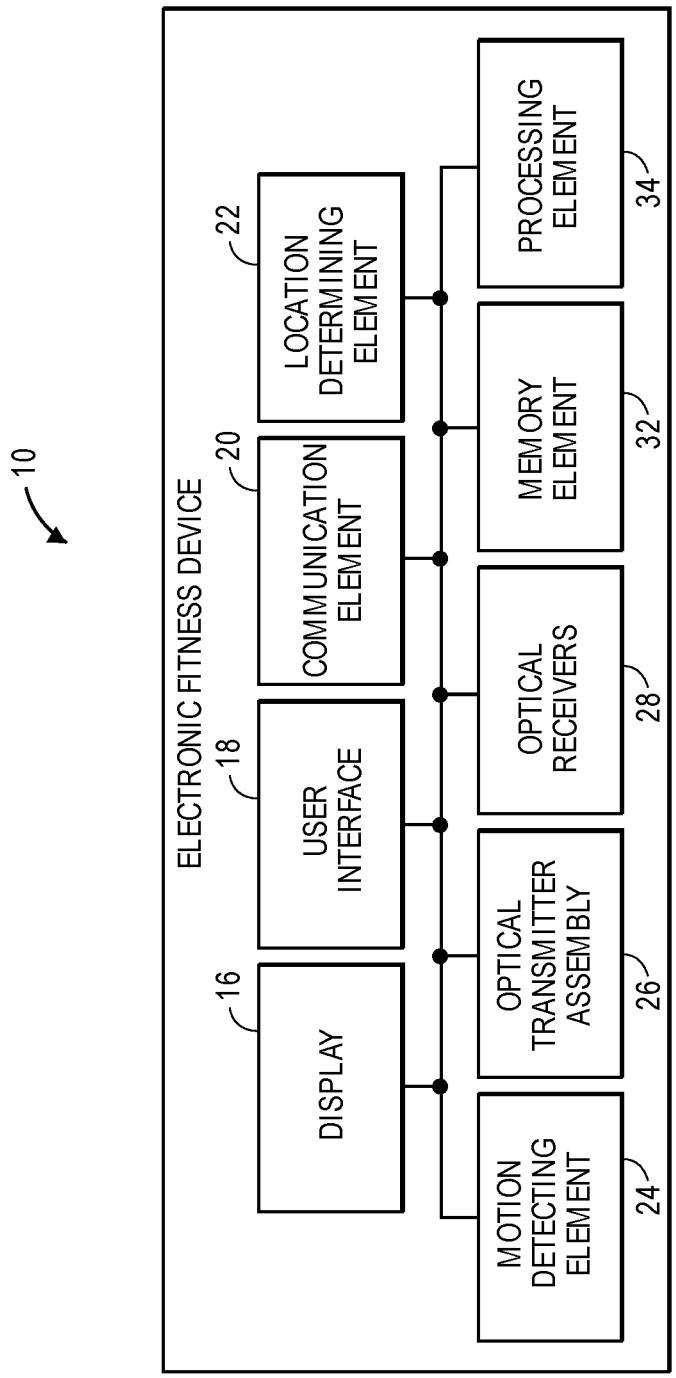
FIG. 10 is a schematic block diagram of various electronic components of the electronic fitness device.

Referring to FIG. 9, and FIG. 10, the processing element 34 may remove a DC component of the reference PPG signal and analyze the reference PPG signal (PPG REF) to determine various characteristics of the reference PPG signal and store the determined signal characteristics in memory element 32. For example, a signal analysis element 52 of the processing element 34 may determine a reference frequency, a reference bandwidth, a reference amplitude, a reference phase, reference maximum value times, reference minimum value times, reference zero crossing times, and the like, of the reference PPG signal. These determined signal characteristics may be used by a signal process for the processing and conditioning of other PPG signals (PPG 2-PPG n) with a lower SNR and/or SMNR resulting from optical signals having other wavelengths where the absorption of the optical signal by the blood is relatively low. The signal processor may include a bandpass filter 54 with a center pass frequency at the reference frequency may be implemented and utilized to filter the other PPG signals (PPG 2-PPG n). An amplifier 56 may be utilized to amplify the other PPG signals (PPG 2-PPG n). A phase adjuster 58 may be utilized to shift the phase of other PPG signals (PPG 2-PPG n). A sampler 60 may be implemented to sample the other PPG signals (PPG 2-PPG n) at the determined reference maximum value times, reference minimum value times, and reference zero crossing times because those times likely indicate when the maximum, minimum, and zero-crossing times of the corresponding cardiac component of the other PPG signal (PPG 2-PPG n). As a result, processing element 34 may implement augmented pulse spectroscopy techniques on the reference PPG signal (PPG REF) and the other PPG signals (PPG 2-PPG n) to isolate or filter the cardiac component, CC REF and CC 2-CC n, of each PPG signal generated by an optical receiver based on reflections of optical signals transmitted by one or more optical transmitters. In embodiments, the processing element 34 may determine a reference cardiac component of the reference PPG signal. The processing element may determine a pulse oximetry level (blood oxygen saturation), a pulse-oximetry indicator, a hematocrit level, or a user hydration level based on the reference cardiac component and one or more additional cardiac components, as described herein.

Embodiments of the present technology will now be described in more detail with reference to the drawing figures. Referring initially to FIGS. 1, 3, and 6-15, an electronic fitness device 10 configured to implement the disclosed pulse spectroscopy techniques is illustrated. An exemplary electronic fitness device 10 may be embodied by a smart watch or a fitness band that is typically worn on a user's wrist, but may also be embodied by bands or belts worn on the user's arm, leg, or torso. Other examples of the electronic fitness device 10 may include smartphones, personal data assistants, or the like which include a surface, operable to retain optical devices, that can be pressed against the user's skin. The electronic fitness device 10 may broadly comprise a housing 12, a wrist band 14, a display 16, a user interface 18, a communication element 20, a location determining element 22, a motion detecting element 24, an optical transmitter assembly 26 including one or more optical transmitters 42, an optical receiver(s) 28, a lens(es) 30, a memory element 32, and a processing element 34.

The housing 12 generally houses or retains other components of the electronic fitness device 10 and may include or be coupled to the wrist band 14. As seen in FIG. 3, the housing 12 may include a bottom wall 36, an upper surface 38, and at least one side wall 40 that bound an internal cavity (not shown in the figures). The bottom wall 36 may include a lower, outer surface that contacts the user's wrist while the user is wearing the electronic fitness device 10. The upper surface 38 opposes the bottom wall 36. In various embodiments, the upper surface 38 may further include an opening that extends from the upper surface to the internal cavity. In some embodiments, such as the exemplary embodiments shown in the figures, the bottom wall 36 of the housing 12 may have a round, circular, or oval shape, with a single circumferential side wall 40. In other embodiments, the bottom wall 36 may have a four-sided shape, such as a square or rectangle, or other polygonal shape, with the housing 12 including four or more sidewalls. The bottom wall 36 includes one or more openings through which one or more optical transmitters 42 of the optical transmitter array (s) 26 emit or transmit an optical signal and one or more optical receiver(s) 28 receive reflections of the optical signal from the user's skin. The one or more openings within the bottom wall 36 may be covered by one or more lenses 30 through which the optical signal may be transmitted and received.

The display 16 generally presents the information mentioned above, such as time of day, current location, and the like. The display 16 may be implemented in one of the following technologies: light-emitting diode (LED), organic LED (OLED), Light Emitting Polymer (LEP) or Polymer LED (PLED), liquid crystal display (LCD), thin film transistor (TFT) LCD, LED side-lit or back-lit LCD, or the like, or combinations thereof. In some embodiments, the display 16 may have a round, circular, or oval shape. In other embodiments, the display 16 may possess a square or a rectangular aspect ratio which may be viewed in either a landscape or a portrait orientation.

The user interface 18 generally allows the user to directly interact with the electronic fitness device 10 and may include pushbuttons, rotating knobs, or the like. In various embodiments, the display 16 may also include a touch screen occupying the entire display 16 or a portion thereof so that the display 16 functions as at least a portion of the user interface 18. The touch screen may allow the user to interact with the electronic fitness device 10 by physically touching, swiping, or gesturing on areas of the display 16.

The communication element 20 generally allows communication with external systems or devices. The communication element 20 may include signal and/or data transmitting and receiving circuits, such as antennas, amplifiers, filters, mixers, oscillators, digital signal processors (DSPs), and the like. The communication element 20 may establish communication wirelessly by utilizing radio frequency (RF) signals and/or data that comply with communication standards such as cellular 2G, 3G, 4G, LTE, or 5G, Institute of Electrical and Electronics Engineers (IEEE) 802.11 standard such as Wi-Fi, IEEE 802.16 standard such as WiMAX, Bluetooth™, or combinations thereof. In addition, the communication element 20 may utilize communication standards such as ANT, ANT+, Bluetooth™ low energy (BLE), the industrial, scientific, and medical (ISM) band at 2.4 gigahertz (GHz), or the like. Alternatively, or in addition, the communication element 20 may establish communication through connectors or couplers that receive metal conductor wires or cables which are compatible with networking technologies such as Ethernet. In certain embodiments, the communication element 20 may also couple with optical fiber cables. The communication element 20 may be in electronic communication with the memory element 32 and the processing element 34.

The location determining element 22 generally determines a current geolocation of the electronic fitness device 10 and may receive and process radio frequency (RF) signals from a global navigation satellite system (GNSS) such as the global positioning system (GPS) primarily used in the United States, the GLONASS system primarily used in the Soviet Union, or the Galileo system primarily used in Europe. The location determining element 22 may accompany or include an antenna to assist in receiving the satellite signals. The antenna may be a patch antenna, a linear antenna, or any other type of antenna that can be used with location or navigation devices. The location determining element 22 may include satellite navigation receivers, processors, controllers, other computing devices, or combinations thereof, and memory. The location determining element 22 may process a signal, referred to herein as a "location signal", from one or more satellites that includes data from which geographic information such as the current geolocation is derived. The current geolocation may include coordinates, such as the latitude and longitude, of the current location of the electronic fitness device 10. The location determining element 22 may communicate the current geolocation to the processing element 34, the memory element 32, or both.

Although embodiments of the location determining element 22 may include a satellite navigation receiver, it will be appreciated that other location-determining technology may be used. For example, cellular towers or any customized transmitting radio frequency towers can be used instead of satellites may be used to determine the location of the electronic fitness device 10 by receiving data from at least three transmitting locations and then performing basic triangulation calculations to determine the relative position of the device with respect to the transmitting locations. With such a configuration, any standard geometric triangulation algorithm can be used to determine the location of the electronic fitness device 10. The location determining element 22 may also include or be coupled with a pedometer, accelerometer, compass, or other dead-reckoning components which allow it to determine the location of the device 10. The location determining element 22 may determine the current geographic location through a communications network, such as by using Assisted GPS (A-GPS), or from another electronic fitness device. The location determining element 22 may even receive location data directly from a user.

The motion detecting element 24 generally detects movement of the electronic fitness device 10 and may include accelerometers, tilt sensors, inclinometers, gyroscopes, combinations thereof, or other devices including piezoelectric, piezoresistive, capacitive sensing, or micro electromechanical systems (MEMS) components. The motion detecting element 24 may sense motion along one axis of motion or multiple axes of motion. Motion detecting element 24 may sense motion along three orthogonal axes, such as X, Y, and Z. In various embodiments, the motion detecting element 24 may measure the acceleration, such as acceleration due to the gravitation (G) force, of the user and may output the measured data in a motion signal having a digital binary format.

In embodiments, the optical transmitter array(s) 26 include a first optical transmitter array 26A and a second optical transmitter array 26B. Each optical transmitter array 26 includes a plurality of optical transmitters 42 (each optical transmitter 42 indicated in FIGS. 11 and 12 with a "TX" prefix). In some embodiments, each optical transmitter 42 may include a photonic generator, such as a light-emitting diode (LED), a modulator, a top emitter, an edge emitter, or the like. The photonic generator receives an electrical input signal from the processing element 34 that may be a control signal, such as an electric voltage or electric current that is analog or digital, or data, either of which is indicative of activating or energizing the optical transmitter 42 to transmit (emit) an optical signal having a desired amplitude, frequency, and duration. The photonic generator of each optical transmitter 42 transmits electromagnetic radiation having a particular wavelength (the optical signal) in the visible light spectrum, which is typically between approximately 400 nanometers (nm) to 700 nm, or in the infrared spectrum, which is typically between approximately 700 nm to 1 millimeter (mm). However, in some embodiments, the photonic generator transmits electromagnetic radiation in wavelength range of 1000 nm to 1500 nm. The wavelength of the optical signal is generally determined by, or varies according to, the material from which the photonic generator of each optical transmitter 42 is formed. The optical signal may comprise a sequence of pulses, a periodic or non-periodic waveform, a constant level for a given period of time, or the like, or combinations thereof. In other embodiments, each optical transmitter 42 may include a driver circuit, with electronic circuitry such as amplifier and an optional filter, electrically coupled to the photonic generator. The driver circuit may receive the electrical input signal (control signal) from the processing element 34 and the driver circuit may generate an electric voltage or electric current to the photonic generator, which in turn, transmits (emits) the optical signal.

The first optical transmitter array 26A may include four optical transmitters 42: a first optical transmitter 42A1 configured or operable to transmit an optical signal having a first wavelength ($\lambda 1$), a second optical transmitter 42A2 configured or operable to transmit an optical signal having a second wavelength ($\lambda 2$), a third optical transmitter 42A3 configured or operable to transmit an optical signal having a third wavelength ($\lambda 3$), and a fourth optical transmitter 42A4 configured or operable to transmit an optical signal having a fourth wavelength ($\lambda 4$). In various embodiments, the processing element 34 may utilize each wavelength to perform a certain function, as shown in FIGS. 13-15, using a PPG signal generated by one or more optical receiver(s) 28 that receive reflections of each optical signal from the user's skin.

In an exemplary embodiment, the processing element 34 may output a control signal to: an optical transmitter configured to transmit an optical signal having the first wavelength, the reflection of which provides a PPG signal to the processing element 34 enabling an accurate determination of the user's heart rate in the range from approximately 520 nm to approximately 580 nm; an optical transmitter configured to transmit an optical signal having the second wavelength, the reflection of which amplifies the motion component of the PPG signal relative to the cardiac component to enable isolation of the motion component, in the range from approximately 660 nm to approximately 700 nm; an optical transmitter configured to transmit an optical signal having the third wavelength, the reflection of which provides a first PPG signal to the processing element 34 for use with determining a pulse oximetry in the red range of the spectrum from approximately 620 nm to approximately 660 nm; and an optical transmitter configured to transmit an optical signal having the fourth wavelength, the reflection of which provides a second PPG signal to the processing element 34 for use with determining a pulse oximetry in the infrared range of the spectrum from approximately 850 nm to approximately 940 nm. In embodiments, specific exemplary wavelengths may include approximately 540 nm for the first wavelength, approximately 680 nm for the second wavelength, approximately 660 nm for the third wavelength, and approximately 940 nm for the fourth wavelength.

Each optical transmitter 42 of the first optical transmitter array 26A may be integrated on a single substrate, such as a printed circuit board, or may be positioned in close proximity to one another. Generally, the optical transmitters 42 are oriented or located to form a linear array, as shown in FIGS. 13-15, although the relative positioning of each optical transmitter 42 within the array maybe rearranged and still remain within the scope of the present technology. The first optical transmitter array 26A is positioned in an opening on the bottom wall 36 of the housing 12 and may be positioned under a lens 30. In some embodiments, each optical transmitter 42 may be positioned in its own opening of the bottom wall 36.

The second optical transmitter array 26B may include two optical transmitters 42: a first optical transmitter 42B1 configured or operable to transmit an optical signal having a fifth wavelength ($\lambda 5$) and a second optical transmitter 42B2 configured or operable to transmit an optical signal having a sixth wavelength ($\lambda 6$). Similar to the first optical transmitter array 26A, the processing element 34 may utilize wavelengths of the second optical transmitter array 26B to perform a certain function, as shown in FIGS. 13-15, using a PPG signal generated by one or more optical receiver(s) 28 that receive reflections of each optical signal from the user's skin. In an exemplary embodiment, the processing element 34 may output a control signal to: an optical transmitter configured to transmit an optical signal having the fifth wavelength, the reflection of which provides a PPG signal to the processing element 34 enabling an accurate determination of the user's heart rate in the range from approximately 520 nm to approximately 580 nm; and an optical transmitter configured to transmit an optical signal having the sixth wavelength, the reflection of which provides a PPG signal to the processing element 34 enabling isolation of the motion component of the PPG signal in the range from approximately 660 nm to approximately 700 nm.

Each of optical transmitters 42 of the second optical transmitter array 26B may be integrated on a single substrate, such as a printed circuit board, or may be positioned in close proximity to one another. The second optical transmitter array 26B is positioned in an opening on the bottom wall 36 of the housing 12 and may be positioned under a lens 30. In some embodiments, each optical transmitter 42 may be positioned in its own opening of the bottom wall 36. At any rate, the second optical transmitter array 26B is separated from the first optical transmitter array 26A by a first distance. In various embodiments, the longitudinal axis line (through the center of each optical transmitter 42) of the first optical transmitter array 26A is parallel to the longitudinal axis line of the second optical transmitter array 26B.

In some embodiments, as shown in FIG. 13, the first wavelength and the fifth wavelength may be substantially equal and the second wavelength and the sixth wavelength may be substantially equal. Therefore, the wavelengths of one or more optical transmitters 42 of the second optical transmitter array 26B may duplicate some of the functionality of one or more optical transmitters 42 of the first optical transmitter array 26A, but given that the optical signals transmitted from the second optical transmitter array 26B follow a different path in comparison to the optical signals transmitted from the first optical transmitter array 26A, there is signal path differentiation or diversity between the optical signals. As detailed herein, the processing element 34 may utilize the plurality of optical signals, which provide signal path diversity, to more accurately determine the user's heart rate, pulse oximetry level, and other blood-related and cardiac information. The processing element 34 may utilize each wavelength to perform a certain function identified in FIGS. 5A and 5B. The processing element 34 may determine a heart rate using a PPG signal generated by optical receivers 28A and/or 28B based on reflections of an optical signal received from the user's skin that had originated from optical transmitters 42A1 and/or 42B1. Similarly, the processing element 34 may determine a pulse oximetry level using a PPG signal generated by optical receivers 28A and/or 28B based on reflections of an optical signal received from the user's skin that had originated from optical transmitters 42A3 and/or 42A4. The processing element 34 may also utilize a PPG signal generated by optical receivers 28A and/or 28B based on reflections of an optical signal, which has the second wavelength that is substantially equal to the sixth wavelength, originating from optical transmitters 42A2 and/or 42B2 to isolate a motion component from the PPG signal and reduce or minimize the motion component from other PPG signals resulting from optical signals having other wavelengths.

In other embodiments, as shown in FIG. 14, the first wavelength and the second wavelength may be substantially different and each may be different than the fifth wavelength and the sixth wavelength. Therefore, the wavelengths of one or more optical transmitters 42 of the second optical transmitter array 26B are utilized to provide different functionality than the one or more optical transmitters 42 of the first optical transmitter array 26A. There is signal path differentiation or diversity between the optical signals in such embodiments. The optical signals transmitted from the first optical transmitter array 26A may pass to both the first optical receiver 28A and the second optical receiver 28B. Similarly, the optical signals transmitted from the second optical transmitter array 26B may also pass to both the first optical receiver 28A and the second optical receiver 28B. As detailed herein, the processing element 34 may utilize the plurality of optical signals, which provide signal path diversity, to more accurately determine the user's heart rate, pulse oximetry level, hematocrit, and other blood-related and cardiac information. The processing element 34 may utilize each wavelength to perform a certain function identified in FIGS. 5A and 5B. The processing element 34 may determine a heart rate using a PPG signal generated by optical receivers 28A and/or 28B based on reflections of an optical signal received from the user's skin that had originated from optical transmitter 42B2. Similarly, the processing element 34 may determine a pulse oximetry level using a PPG signal generated by optical receivers 28A and/or 28B based on reflections of an optical signal received from the user's skin that had originated from optical transmitters 42A3 and 42A4. The processing element 34 may determine a hematocrit level using a PPG signal generated by optical receivers 28A and/or 28B based on reflections of an optical signal received from the user's skin that had originated from optical transmitters 42A1 and 42A2.

In other embodiments, as shown in FIG. 15, the electronic fitness device 10 may include a first optical transmitter array 26A, a first optical transmitter 42B1, and an optical receiver 28A. The wavelength of an optical signal emitted by each optical transmitter may be unique. As detailed herein, the processing element 34 may utilize the plurality of optical signals, which provide signal path diversity, to more accurately determine the user's heart rate, pulse oximetry level, hematocrit, and other blood-related and cardiac information. The processing element 34 may utilize each wavelength to perform a certain function identified in FIGS. 5A and 5B. The processing element 34 may determine a heart rate using a PPG signal generated by optical receiver 28A based on reflections of an optical signal received from the user's skin that had originated from optical transmitter 42B1. Similarly, the processing element 34 may determine a pulse oximetry level using a PPG signal generated by optical receiver 28A based on reflections of an optical signal received from the user's skin that had originated from optical transmitters 42A1 and 42A3. The processing element 34 may determine a hematocrit level using a PPG signal generated by optical receiver 28A based on reflections of an optical signal received from the user's skin that had originated from optical transmitters 42A1 and/or 42A2. In such embodiments, the processing element 34 may utilize a wavelength to perform multiple functions. As shown in FIG. 15, the optical signal transmitted by optical transmitter 42A1 may be utilized to determine a pulse oximetry level and a hematocrit level. The wavelength of the optical signal transmitted by optical transmitter 42A1 may be any overlapping wavelength (850 nm-900 nm) of the "pulse ox 2" band of FIG. 5A (850 nm-950 nm) and the "hematocrit 1" band of FIG. 5B (800 nm-900 nm).

Figure 11:
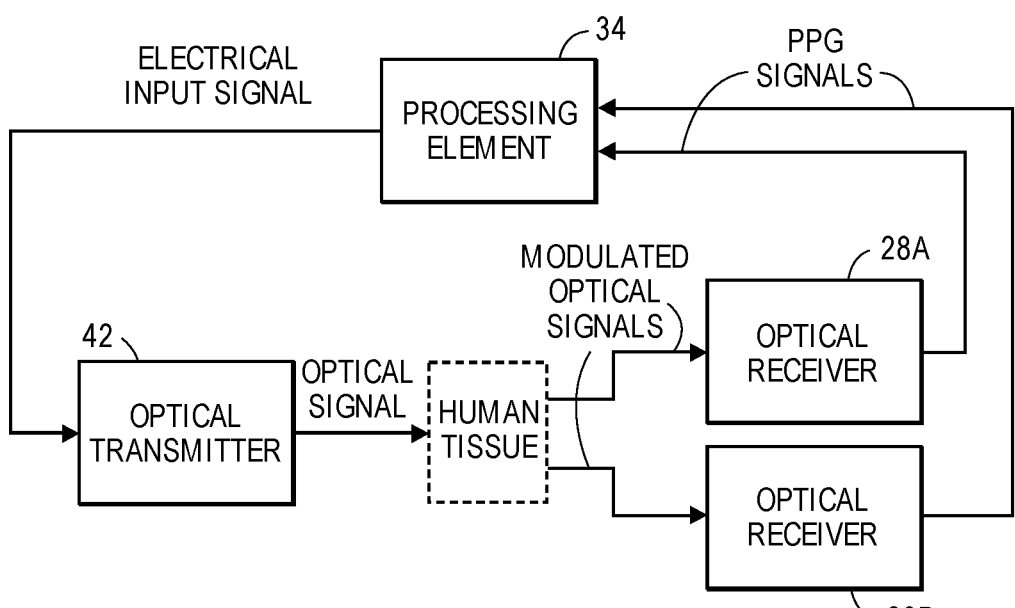
FIG. 11 is a schematic block diagram illustrating the electronic components involved in emitting a plurality of optical signals, receiving reflections of the plurality of optical signals, and generating a PPG signal corresponding to each optical signal.

The electronic fitness device 10 may include a first optical receiver 28A and a second optical receiver 28B (each optical receiver 28 indicated in FIGS. 11 and 12 with the "RX" prefix). In some embodiments, each optical receiver 28 may include a photodetector, such as a photodiode, a phototransistor, a photoresistor, a phototube, or the like. The photodetector receives electromagnetic radiation having multiple wavelengths (typically any of the wavelengths generated by the photonic generators) and in response, generates a PPG signal, comprising an electric current, an electric voltage, or other electrical parameter, that corresponds to the intensity of the modulated optical signal in amplitude and frequency that is transmitted by an optical transmitter 42 and reflected from the user's skin. Given that the optical receivers 28 may receive multiple optical signals, each having a particular wavelength, each PPG signal generated by either optical receiver 28 may be a particular wavelength-related PPG signal because it includes characteristics or components resulting from, or related to, the particular wavelength of the optical signal transmitted (emitted) by an optical transmitter 42 of the first or second optical transmitter arrays 26A, 26B. In other embodiments, each optical receiver 28 may include the photodetector electrically coupled to an amplifier circuit followed by an analog-to-digital converter (ADC). The photodetector may receive electromagnetic radiation having multiple wavelengths and in response, may generate an output signal, comprising an electric current, an electric voltage, or other electrical parameter that corresponds to the intensity of the modulated optical signal in amplitude and frequency that is transmitted by an optical transmitter 42 and reflected from the user's skin. The amplifier circuit may receive the output signal from the photodetector and amplify it to produce an amplified output signal that is analog and communicated to the ADC. The ADC may sample the amplified output signal and output a PPG signal, which is converted into a corresponding stream of digital data.

Each optical receiver 28 may generate a plurality of PPG signals, each PPG signal resulting from an optical signal transmitted by one of the optical transmitters 42 of the first or second optical transmitter arrays 26A, 26B. In embodiments having a plurality of optical receivers 28, for example, the first optical receiver 28A may generate a first PPG signal resulting from the optical signal received from the first optical transmitter 42, a second PPG signal resulting from the optical signal received from the second optical transmitter 42, and so forth. Likewise, the second optical receiver 28B may generate a first PPG signal resulting from the optical signal received from the first optical transmitter 42, a second PPG signal resulting from the optical signal received from the second optical transmitter 42, and so forth. Alternatively, the first optical receiver 28A may generate a first PPG signal resulting from the optical signal received from the first optical transmitter 42, while the second optical receiver 28B may generate a second PPG signal resulting from the optical signal received from the first optical transmitter 42, and so forth.

The optical receiver 28 is typically a photodiode and may be any other device configured to generate a PPG signal based on the intensity of light received by a sensor element. The first optical receiver 28A is positioned in an opening on the bottom wall 36 of the housing 12 between the first optical transmitter array 26A and the second optical transmitter array 26B, while the second optical receiver 28B may be positioned in an opening on the bottom wall 36 on the opposing side of either the second optical transmitter array 26B (as shown in FIGS. 11 and 12) or the first optical transmitter array 26A (not shown).

In some implementations, the housing 12 and wrist band 14 may be positioned such that the optical components (optical transmitter array(s) 26 and optical receiver(s) 28) are positioned substantially over (i.e. most proximally to) one of the user's wrist bones. For example, the optical components may be positioned substantially over the ulna bone or substantially over the radius bone.

The electronic fitness device 10 may include a first lens 30A, a second lens 30B, a third lens 30C, and a fourth lens 30D. One or more openings within the bottom wall 36 may be covered by the first lens 30A, the second lens 30B, the third lens 30C, and the fourth lens 30D such that the optical signals may be transmitted and received through each lens 30. The lenses 30 generally provide cover for the optical transmitters 42 and the optical receivers 28. In addition, the lenses 30 may be configured, operable, shaped, or formed to provide focusing, collimation, refraction, diffraction, and so forth. Furthermore, some lenses 30, such as the lenses 30 that cover the optical transmitters 42, may provide some functions, while other lenses 30, such as the lenses 30 that cover the optical receivers 28, may provide other functions. The lenses 30 that cover the optical transmitters 42 may direct optical signals transmitted by the optical transmitters 42 to the skin of the user. The lenses 30 that cover the optical receivers 28 may direct the optical signals reflected from the skin to the optical receivers 28. The lenses 30 may be constructed from glass, polymers, or the like. The first lens 30A may cover the first optical transmitter array 26A, the second lens 30B may cover the first receiver 28A, the third lens 30C may cover the second optical receiver 28B, and the fourth lens 30D may cover the second optical transmitter array 26B. In various embodiments, all of the lenses 30 may be the same size and shape and may be aligned with one another on the bottom wall 36. In addition, one surface of each lens 30 may be coupled to an outer surface of the bottom wall 36 of the housing 12.

The memory element 32 may be embodied by devices or components that store data in general, and digital or binary data in particular, and may include exemplary electronic hardware data storage devices or components such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory element 32 may be embedded in, or packaged in the same package as, the processing element 34. The memory element 32 may include, or may constitute, a "computer-readable medium". The memory element 32 may store the instructions, code, code statements, code segments, software, firmware, programs, applications, apps, services, daemons, or the like that are executed by the processing element 34. The memory element 32 may also store settings, data, documents, sound files, photographs, movies, images, databases, and the like.

The processing element 34 may include electronic hardware components such as processors, microprocessors (single-core or multi-core), microcontrollers, digital signal processors (DSPs), field-programmable gate arrays (FPGAs), analog and/or digital application-specific integrated circuits (ASICs), or the like, or combinations thereof. In some embodiments, the processing element 34 may also include ADC circuitry. The processing element 34 may generally execute, process, or run instructions, code, code segments, code statements, software, firmware, programs, applications, apps, processes, services, daemons, or the like. The processing element 34 may also include hardware components such as finite-state machines, sequential and combinational logic, and other electronic circuits that can perform the functions necessary for the operation of the current invention. In various embodiments, the processing element 34 may include multiple computational components and functional blocks that are packaged separately but function as a single unit. The processing element 34 may be in electronic communication with the other electronic components through serial or parallel links that include universal busses, address busses, data busses, control lines, and the like. Furthermore, the processing element 34 may include multiple physically separated but logically and electronically connected functional blocks.

The processing element 34 may configure a plurality of filters to filter PPG signals having a low SNR and/or SMNR resulting from optical signals having other wavelengths where the absorption of the optical signal by pulsatile blood in the skin or tissue is low based on signal filter parameters and/or signal characteristics determined for one or more PPG signals. Referring to FIGS. 6-9, the processing element 34 may further include, or be in electronic communication with a filter, such an active filter 44 utilized to perform correlated pulse spectroscopy and/or a filter 54 utilized to perform augmented pulse spectroscopy, or may be configured or programmed to perform active filtering functions, to analyze and removed undesired components of PPG signals.

Figure 6:
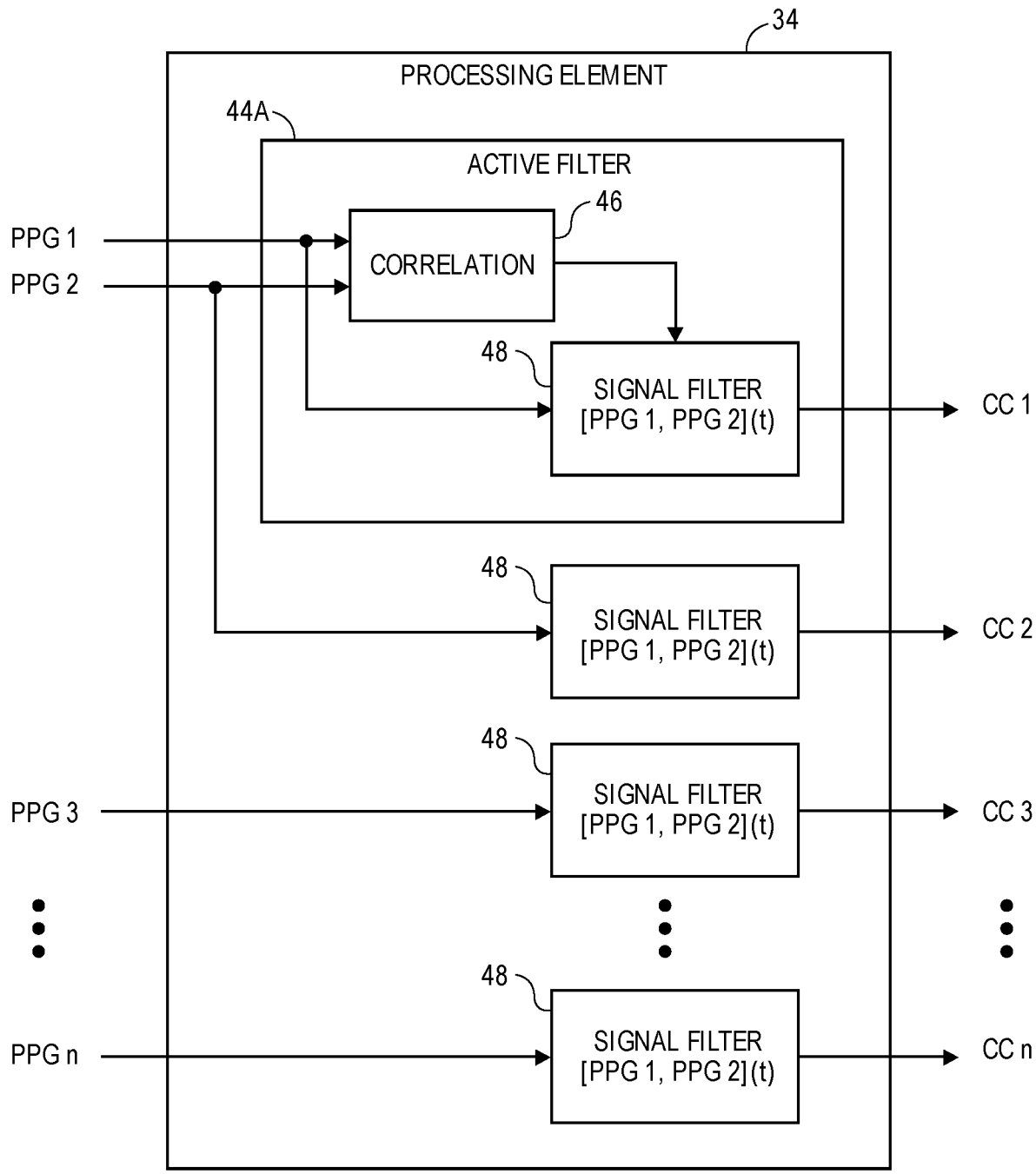
FIG. 6 is a schematic block diagram of one embodiment of a processing element for performing correlated pulse spectroscopy.
Figure 7:
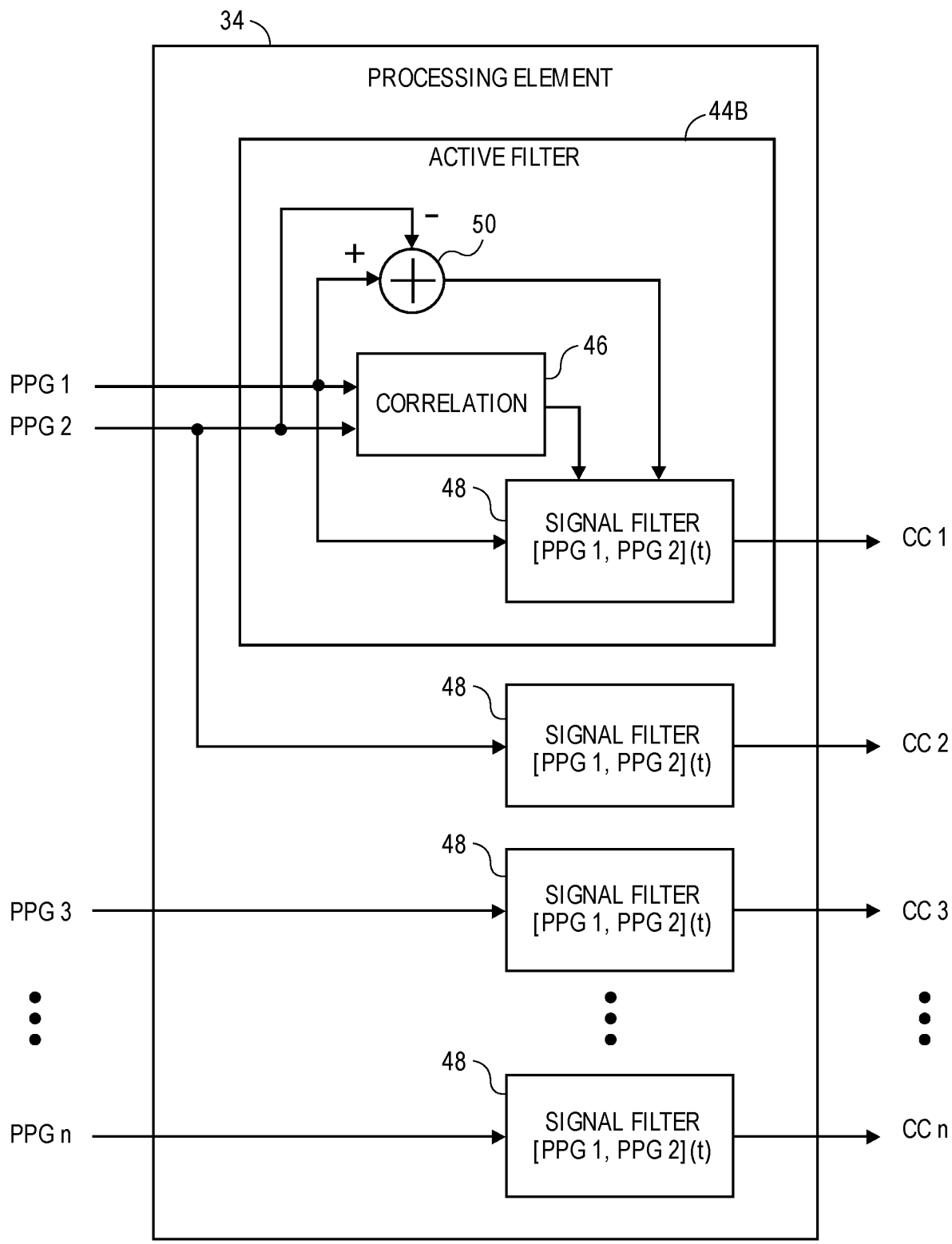
FIG. 7 is a schematic block diagram of another embodiment of a processing element for performing correlated pulse spectroscopy.
Figure 8:
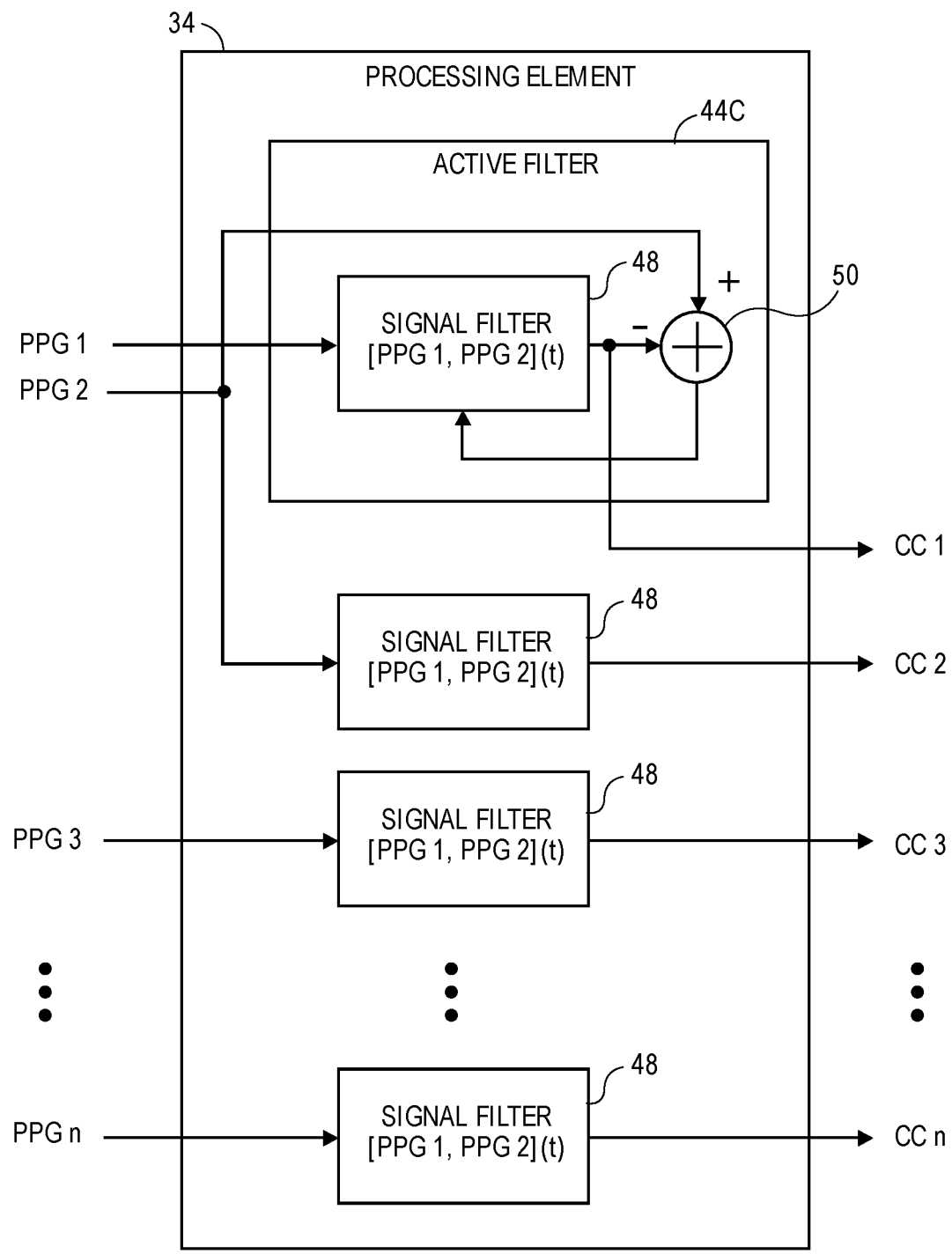
FIG. 8 is a schematic block diagram of yet another embodiment of a processing element for performing correlated pulse spectroscopy.

When implementing correlated pulse spectroscopy, as shown in FIGS. 6-8, the active filter 44 generally compares two PPG signals in order to determine a plurality of signal filter parameters which are utilized to maintain and/or adjust the operating parameters for a plurality of signal filters 48. An exemplary signal filter 48 may include a discrete-time, multi-tap time delay line filter, such as a finite impulse response (FIR) filter or an infinite impulse response (IIR) filter, wherein each tap includes a filter coefficient. The values of the filter coefficients may be determined by any of the signal filter parameters. Typically, the configuration of the signal filter 48 and the values of the filter coefficients are chosen (and adjusted) to perform a band-pass filter function. The values of the filter coefficients are updated or adjusted on a continuous and/or periodic basis. In the discrete-time domain, the values of the filter coefficients are updated or adjusted every time period. When used in filtering the PPG signals, the signal filter 48 is configured and the values of the filter coefficients are chosen (and adjusted) to band-pass the PPG signal at a pass band frequency at approximately the fundamental frequency of the cardiac component of the PPG signal. Thus, the signal filter 48 may generate the cardiac component when it receives a PPG signal.

In one embodiment, shown in FIG. 6, the active filter 44A includes a correlation unit 46 and a signal filter 48. The correlation unit 46 includes a first signal input, a second signal input, and a signal output. The first and second inputs receive first and second PPG signals respectively. The correlation unit 46 performs a correlation, such as a cross correlation, on the two PPG signals and generates an output that includes the contents of the two correlated signals that are common to, or included in, both PPG signals. Generally, other contents or components, such as noise, that are not common to both signals are effectively filtered out. Given that the signals are PPG signals generated based on reflections of optical signals reflected from the user's skin or tissue, the signal content that is common to, or included in, both PPG signals includes the cardiac component, as shown in FIG. 4. Thus, the signal output of the correlation unit 46 is or includes a common cardiac component.

The common cardiac component is utilized to determine a plurality of signal filter parameters to be utilized with configuring one or more signal filters 48. For example, in embodiments, one signal filter parameter is a representation, or model, of the common cardiac component, such as at least a complete period of a common cardiac component waveform represented in the time domain. Additionally, or alternatively, the common cardiac component may be represented in the frequency domain by performing a time domain to frequency domain transform, such as a DFT or other transform. The common cardiac component may also or instead be represented through transforms such as a discrete wavelet transform or similar mathematical operations. In other embodiments, another signal filter parameter is a plurality of spectral parameters of the cardiac component, such as the fundamental frequency, harmonic frequencies, bandwidth, and the like. In other embodiments, a signal filter parameter is a filter coefficient determined by performing a transfer function using either the first PPG signal and/or the second PPG signal as an input function and the common cardiac component as an output function. The signal filter parameters are stored in the memory element 32 and are updated on a continuous and/or periodic basis as the first and second PPG signals are received. Any one or more of the signal filter parameters are utilized to maintain and/or adjust the operating parameters, such as pass frequency ranges, bandwidths, etc. for the signal filter 48.

Each signal filter 48 generally performs a filtering function, such as high-pass, low-pass, band-pass, band-cut (notch), etc., on a signal—in this case, a PPG signal. The operation and performance of the signal filter 48 may be determined or controlled by the signal filter parameters. In embodiments, the signal filter 48 may filter a PPG signal using the one or more signal filter parameters (e.g., comparing a third PPG signal to the time domain waveform of the common cardiac component in order to generate the cardiac component of the third PPG signal, comparing the third PPG signal to the frequency domain model of the common cardiac component in order to generate the cardiac component of the third PPG signal, etc.). Additionally, or alternatively, in some embodiments, the signal filter 48 may be a band-pass filter used to filter a third PPG signal using a pass band frequency determined by the spectral parameters or the frequency domain transform of the first and second PPG signals. Additionally, or alternatively, the signal filter 48 may perform the transfer function on the third PPG signal. The signal filter 48 may be labeled in the figures as a function of the first and second PPG signals: "[PPG 1, PPG 2](t)".

In another embodiment, shown in FIG. 7, the processing element 34 includes an active filter 44B including the correlation unit 46, a first signal filter 48, and a signal adder 50. The active filter 44B operates in a substantially similar fashion to the active filter 44A, except that the processing element 34 determines the signal filter parameter based on an output of the signal adder 50 as well as an output of the correlation unit 46. The signal adder 46 includes a positive input that receives a first PPG signal, a negative input that receives a second PPG signal, and an output, which outputs a signal that is a difference of the first and second PPG signals received by the positive input and the negative input because the negative input is negated or inverted, as shown in FIG. 7. Subsequently, the processing element 34 may determine the same signal filter parameters discussed above for FIG. 6 based on a difference between the two PPG signals and utilize the determined signal parameters to configure one or more additional signal filters 48.

In yet another embodiment, shown in FIG. 8, the processing element 34 includes an active filter 44C including a first signal filter 48 and a signal adder 50. The active filter 44C may be constructed, or electrically connected, in an adaptive filter configuration. That is, the first signal filter 48 receives one of the PPG signals (the first PPG signal), while the other signal (the difference signal) is received from the output of the signal adder 50. A positive input of the signal adder 50 receives a first PPG signal and a negative input of the signal adder 50 receives the output of the first signal filter 48, which is the filtered first PPG signal. The output signal of the adder 50, which is the difference between the second PPG signal and the first correlated component, is received by the first signal filter 48 as a feedback signal. In the adaptive filter configuration, the processing element 34 controls the first signal filter 48 to employ an adaptive function to update the values of the signal filter parameters on a continuous and/or periodic basis, such as every discrete-time domain time period. An example of the adaptive function includes a least mean squares algorithm which adjusts the values of the coefficients based on the content of the input PPG signal, a convergence factor, and the feedback signal from the signal adder 50. By utilizing the adaptive function, the first signal filter 48 filters the first PPG signal in order to find the components in the first PPG signal that are included in the second PPG signal. Thus, the first signal filter 48 of the active filter 44 generates a correlated component of the first PPG signal, which is substantially the first cardiac component. Subsequently, the processing element 34 may determine the same signal filter parameters discussed above for FIG. 6 based on the cardiac component of the first PPG signal and utilize the determined signal parameters to configure one or more additional signal filters 48.

As shown in FIGS. 6-8, the processing element 34 includes a plurality of additional signal filters 48, outside the active filters 44A, 44B, 48C, that are configured using one or more signal filter parameters determined using the active filters 44A, 44B, 48C. In certain embodiments, the processing element 34 may include one additional signal filter 48 for each optical signal wavelength the optical transmitters 42 are capable of generating such that at least one PPG signal is generated by an optical receiver 28 based on received reflections of each optical signal. The additional signal filters 48 may each include the same configuration and signal filter parameters as used to configure the signal filter 48 included in the active filter 44, and therefore, they all perform, operate, and function in the same fashion as the first signal filter 48 included in the active filter 44. Thus, processing element 34 may configure a plurality of signal filters 48 to filter PPG signals having a low SNR and/or SMNR resulting from optical signals having other wavelengths where the absorption of the optical signal by pulsatile blood in the skin or tissue is low by determining and using signal filter parameters.

When implementing augmented pulse spectroscopy, as shown in FIG. 9, the processing element 34 may also include, or be in electronic communication with, a signal analysis element 52, and a signal processing element 62, or may be configured or programmed to perform signal analysis functions on PPG signals. The signal analysis element 52 may determine and record various signal characteristics of a reference PPG signal. For example, the processing element 34 may determine and record in the memory element 32 a reference frequency, a reference bandwidth, a reference amplitude, a reference phase, reference maximum value times, reference minimum value times, reference zero crossing times, and the like. The processing element 34 may use these signal characteristics to develop functional units of the signal processing element 62 for the processing and conditioning of other PPG signals with a low SNR and/or SMNR resulting from optical signals having other wavelengths where the absorption of the optical signal by pulsatile blood in the skin or tissue is low.

The functional units of the signal processing element 62 include, among others, a filter 54, an amplifier 56, a phase adjuster 58, and a sampler 60. The filter 54 may be a band-pass filter, such as an FIR or IIR filter, with a center pass frequency at the reference frequency and a bandwidth approximately equal to the reference bandwidth. The amplifier 56 may be a current, voltage, transimpedance, or transconductance amplifier with a single stage or multiple stages. The amplifier 56 may use the reference amplitude or other factors to set its level of gain. The phase adjuster 58 may include analog and/or digital electronic circuitry for signal delaying or phase shifting and may be utilized to adjust the phase of other PPG signals to that of the reference phase. The sampler 60 may include an analog-to-digital converter (ADC) or other signal sampling electronic circuitry that can sample a signal, such as the PPG signal, at specific times. For example, the sampler 60 may sample PPG signals PPG 2-PPG n at the reference maximum value times, the reference minimum value times, the reference zero crossing times, and so forth since those times likely indicate where the cardiac component is maximized compared to noise components and easily determined. Any one or more of these functional units may be utilized on the reference PPG signal and the other PPG signals to generate the cardiac component of each one. Thus, the processing element 34 may configure a plurality of signal filters 48 to filter PPG signals having a low SNR and/or SMNR resulting from optical signals having other wavelengths where the absorption of the optical signal by pulsatile blood in the skin or tissue is low by determine and using signal characteristics of a reference PPG signal.

As shown in FIG. 11, the processing element 34 may be operable, configured, or programmed to perform correlated pulse spectroscopy and augmented pulse spectroscopy by using hardware, software, firmware, or combinations thereof. The processing element 34 may generate an electrical input signal or control signal and communicate it to one or more optical transmitters 42 causing the optical transmitters 42 to emit an optical signal. The processing element 34 receives from the optical receivers 28A and/or 28B one or more PPG signals based on received reflections of the optical signal from the user's skin or tissue. In some embodiments, the processing element 34 may sample the analog PPG signal received from the optical receivers 28A and/or 28B to produce a digital form of the PPG signal as a stream of samples. In other embodiments, the processing element 34 may receive the digital form of the PPG signal from the optical receivers 28A and/or 28B. Given the configuration of the optical transmitters 42 and the optical receivers 28, the optical signal transmitted by any of the optical transmitters 42 may be received by both optical receivers 28A and 28B.

In general, the processing element 34 generates the electrical input signal or control signal and communicates the signal to one or more of the optical transmitters 42 in order to control operation of each optical transmitter 42 within the optical transmitter array(s) 26. The processing element 34 is operable to communicate the electrical input signal or control signal to each optical transmitter 42 individually at different times (sequentially), to one or more groups of the optical transmitters 42 simultaneously, or to all of the optical transmitters 42 simultaneously. The control of the operation of the optical transmitters 42 by the processing element 34 is described in more detail in U.S. patent application Ser. No. 15/860,865, titled "ELECTRONIC FITNESS DEVICE WITH OPTICAL CARDIAC MONITORING", and filed Jan. 3, 2018. The listed patent application is herein incorporated by reference in its entirety.

When performing correlated pulse spectroscopy, the processing element 34 compares two PPG signals that are differentiated in at least one manner. For example, as shown in FIGS. 11-12, the processing element 34 may transmit a control signal to optical transmitter 42A1 and/or 42B1, which may transmit an optical signal having a wavelength corresponding to the "heart rate" band of FIGS. 5A-5B, and receive from optical receiver 28A and/or 28B a PPG signal with a high SNR and/or SMNR. The processing element 34 may also generate the electrical input signal or control signal and communicate it to one or more of any of the other optical transmitters 42 of optical transmitter assembly 26. For example, in embodiments, the processing element 34 may transmit a control signal to optical transmitter 42A2 and/or 42B2, which may transmit an optical signal having a wavelength corresponding to the "motion" band of FIGS. 5A-5B, to optical transmitter 42A3, which may transmit an optical signal having a wavelength corresponding to the "pulse ox 1" band of FIG. 5A, to optical transmitter 42A4, which may transmit an optical signal having a wavelength corresponding to the "pulse ox 2" band of FIG. 5A. Subsequently, the processing element 34 may receive from optical receiver 28A and/or 28B one or more PPG signals having a lower SNR and/or SMNR than PPG signals resulting from optical light having a wavelength corresponding to the "heart rate" band of FIGS. 5A-5B. The processing element 34 may generate additional electrical input signals or control signals that are communicated to the abovementioned optical transmitters 42 to cause corresponding optical signals to be continuously emitted into the user's skin or tissue at a predetermined rate (duty cycle).

As shown in FIGS. 6-8. the first and second PPG signals are received by the active filter 44 which compares the two signals to identify any common components therebetween, such as the common cardiac component. The result of the comparison is utilized to determine a plurality of signal filter parameters. Any or all of the signal filter parameters, such as the time domain model, the frequency domain model, the wavelet transform, etc. of the common cardiac component, may be stored in the memory element 32. At least one of the filter parameters is used to determine and control the operation and performance of the signal filters 48. The first PPG signal is received and filtered by the first signal filter 48 to generate the first cardiac component, the second PPG signal is received and filtered by the second signal filter 48 to generate the second cardiac component, and all other PPG signals are received and filtered by other signal filters 48 to generate a cardiac component within each PPG signal.

In some configurations, the processing element 34 may receive a first PPG signal from the first optical receiver 28A at a first period of time and a second PPG signal from the second optical receiver 28B at a second period of time, such that the first and second optical receivers 28A and 28B are sampled at the same sampling frequency but at two different sets of sampling times to create two differentiated PPG signals. In other configurations, the processing element 34 may sequentially receive a first PPG signal and a second PPG signal from the first optical receiver 28A, such that the two differentiated PPG signals were generated at different times but resulted from optical signals that traveled the same path and have the same wavelength. In still other configurations, the processing element 34 may simultaneously receive a first PPG signal from the first optical receiver 28A and a second PPG signal from the second optical receiver 28B. The processing element 34 may remove the DC component from each of the PPG signals.

When performing augmented pulse spectroscopy, the processing element 34 analyzes a reference PPG signal to determine one or more signal characteristics that are utilized to filter one or more PPG signals. For example, in embodiments, the processing element 34 may transmit a control signal to optical transmitter 42A1 and/or 42B1, which may transmit an optical signal having a wavelength corresponding to the "heart rate" band of FIGS. 5A-5B, and receive from optical receiver 28A and/or 28B a PPG signal with a high SNR and/or SMNR. The processing element 34 may also generate the electrical input signal or control signal and communicate it to one or more of any of the other optical transmitters 42 of optical transmitter assembly 26. For example, the processing element 34 may transmit a control signal to optical transmitter 42A2 and/or 42B2, which may transmit an optical signal having a wavelength corresponding to the "motion" band of FIGS. 5A-5B, to optical transmitter 42A3, which may transmit an optical signal having a wavelength corresponding to the "pulse ox 1" band of FIG. 5A, to optical transmitter 42A4, which may transmit an optical signal having a wavelength corresponding to the "pulse ox 2" band of FIG. 5A. Subsequently, the processing element 34 may receive from optical receiver 28A and/or 28B one or more PPG signals having a lower SNR and/or SMNR than PPG signals resulting from optical light having a wavelength corresponding to the "heart rate" band of FIGS. 5A-5B. The processing element 34 may generate additional electrical input signals or control signals that are communicated to the abovementioned optical transmitters 42 to cause corresponding optical signals to be continuously emitted into the user's skin or tissue at a predetermined rate (duty cycle).

As shown in FIG. 9, the processing element 34 receives the PPG signals from the optical receivers 28A and/or 28B and the processing element 34 may analyze the received PPG signals to determine one or more signal characteristics of the received PPG signals. In embodiments, the processing element 34 may identify and select PPG signal with the greatest SNR and/or SMNR, or any other criteria, as a reference PPG signal. The processing element 34 removes the DC component from the reference PPG signal. The signal analysis element 52 analyzes the reference PPG signal to determine the one or more signal characteristics of the reference PPG signal and stores the determined signal characteristics in the memory element 32. The processing element 34 then utilizes the determined signal characteristics to determine the parameters and settings of the functional units of the signal processing element 62 to process or condition other PPG signals resulting from optical signals having wavelengths that are absorbed poorly by the pulsatile blood in the user's skin or tissue. Any one or more of the functional units of the signal processing element 62 may be utilized to identify the cardiac component from a PPG signal based on the one or more signal characteristics of the reference PPG signal. For example, any of the PPG signals may be input to the filter 54 which filters the signal to generate the cardiac component. In some instances, the functional units of the signal processing element 62 may be used by the processing element 34 in sequential fashion. For example, a PPG signal may first be amplified using amplifier 56, then phase shifted using phase adjuster 58, and then sampled by the sampler 60, before being filtered by the filter 54 to isolate the cardiac component.

As described above, once the processing element 34 is in possession of the cardiac component using either pulse spectroscopy approach, the processing element 34 may determine the user's heart rate as a frequency of the cardiac component (e.g., as a number of beats per minute (bpm)), determine signal characteristics (e.g., maximum values, minimum values, zero crossing, etc.), and determine the user's pulse oximetry by determining the AC and DC values of at least two PPG signals, utilizing the AC and DC values to calculate the pulse oximetry indicator using equation EQ. 1, and using a relationship stored in the memory element 32 associating the pulse oximetry indicator, one or more health characteristics (e.g., age, gender, or weight) and one or more physiological characteristics (e.g., heart rate, blood pressure or heart-rate variability) to a value of the user's pulse oximetry.

The electronic fitness device 10 may operate as follows. The user may desire to determine his blood-related and cardiac information. The processing element 34 may utilize pulse spectroscopy techniques to determine such blood-related and cardiac information. The user may engage the user interface 18 to direct the processing element 34 to begin the process of determining heart rate, pulse oximetry level, hematocrit level, or other blood-related or cardiac information. Alternatively, or additionally, the processing element 34 may have an operating mode in which it automatically initiates the process of determining the user's heart rate, pulse oximetry level, or hematocrit level, when a predetermined event is determined to have occurred (e.g., heart-rate variability exceeding a predetermined threshold, body temperature exceeding a predetermined threshold, etc.) or on a periodic basis (e.g., every second, every minute, hourly, daily, etc.).

In embodiments, the processor may determine an initial heart rate, a pulse oximetry level, and a hematocrit level at the beginning of a fitness activity and subsequent heart rate, pulse oximetry level, and hematocrit levels during and/or after completion of the fitness activity. The processor may then determine a change in the determined levels and utilize stored correlations between changes in heart rate, pulse oximetry level (blood oxygen saturation level (SpO2)), and hematocrit levels (Hct) to determine and provide blood-related and cardiac information, such as a pulse oximetry indicator and a hydration level (Hct) for the user.

In embodiments, the processing element 34 may communicate a first and a second electrical input signal or control signal to the optical transmitter 42 during a first and a second time period, respectively. An optical receiver 28 may receive reflections of transmitted optical signals and generate one or more PPG signals corresponding to the first and second time periods. In other embodiments, the processing element 34 may communicate a first and a second electrical input signal or control signal to a first optical transmitter 42 and a second optical transmitter 42 during a first and a second time period, respectively. An optical receiver 28 may receive reflections of transmitted optical signals and generate one or more PPG signals corresponding to the first and second time periods. In some configurations, a first optical receiver 28A and a second optical receiver 28B receive the reflections of the optical signals, resulting in two PPG signals for the first time period and two PPG signals for the second time period, that are all communicated to the processing element 34. At any rate, the processing element 34 is in possession of two PPG signals and removes the DC component from each signal.

When implementing correlated pulse spectroscopy, the first and second PPG signals are input to the active filter 44, which compares the two signals to one another to identify any common components therebetween (e.g., the common cardiac component, common noise, etc.). The result of the comparison is utilized to determine a plurality of signal filter parameters that are used to determine and control the operation and performance of the signal filters 48. Each signal filter 48 filters a PPG signal received from an optical receiver 28 to identify the cardiac component in each of the PPG signals.

When implementing augmented pulse spectroscopy, one of the PPG signals is identified as a reference PPG signal and is analyzed by a signal analysis element 52 to determine one or more signal characteristics. The signal characteristics are then used to determine the parameters and settings of the functional units of a signal processing element 62 to process or condition the PPG signals in order to identify cardiac components of other PPG signals.

Once cardiac components of a plurality of PPG AC signals have been determined, the processing element 34 may determine the user's heart rate from at least one of the cardiac components, the user's pulse oximetry from the cardiac components and other information from PPG signals resulting from at least two wavelengths, the user's hematocrit from the cardiac components and other information from PPG signals resulting from at least two wavelengths, as discussed above. The display 16 may present the determined blood-related and cardiac information on a one-time or continuous basis as desired by the user.

Although the technology has been described with reference to the embodiments illustrated in the attached drawing figures, it is noted that equivalents may be employed and substitutions made herein without departing from the scope of the technology as recited in the claims.

Having thus described various embodiments of the technology, what is claimed as new and desired to be protected by Letters Patent includes the following:

1. An electronic fitness device comprising:
    a housing including a bottom wall adapted to be positioned over the skin of a user;
    a first optical transmitter positioned along the bottom wall, the first optical transmitter configured to transmit a first optical signal and a second optical signal, the first optical signal having a first wavelength;
    an optical receiver positioned along the bottom wall, the optical receiver configured to receive the first and the second optical signals modulated by the skin of the user and generate first and second photoplethysmogram (PPG) signals resulting from the received first and the second optical signals, respectively, the first and the second optical signals traveling along the same path and each received optical signal containing a cardiac component associated with the user's heartbeat; and a processing element in electronic communication with the first optical transmitter and the optical receiver, the processing element configured to:
control the first optical transmitter to transmit the first optical signal during a first period of time and the second optical signal during a second period of time,
receive the first and the second PPG signals from the optical receiver,
compare the first and the second PPG signals,
identify a common component present in the first and the second PPG signals based on the comparison,
determine a signal filter parameter based on the common component,
generate a first cardiac component from the first PPG signal based on the signal filter parameter,
generate a second cardiac component from the second PPG signal based on the signal filter parameter, and
determine blood-related physiological information based on the first and the second cardiac components.

2. The electronic fitness device of claim 1, further comprising at least a first signal filter and a second signal filter, and wherein the processing element:
generates the first cardiac component by filtering the first PPG signal with the first signal filter using the signal filter parameter, and
generates the second cardiac component by filtering the second PPG signal with the second signal filter using the signal filter parameter.

3. The electronic fitness device of claim 2, further comprising a second optical transmitter positioned along the bottom wall, the second optical transmitter configured to transmit a third optical signal having a second wavelength, wherein the processing element is further configured to:
control the second optical transmitter to transmit the third optical signal during a third period of time,
receive the third PPG signal from the optical receiver, and
filter the third PPG signal with a third signal filter to generate a third cardiac component using the signal filter parameter.

4. The electronic fitness device of claim 1, wherein the processing element is further configured to utilize the signal filter parameter to generate a transfer function that is applied to each of at least a first signal filter and a second signal filter, and wherein the processing element:
generates the first cardiac component by filtering the first PPG signal with the first signal filter, and
generates the second cardiac component by filtering the second PPG signal with the second signal filter.

5. The electronic fitness device of claim 1, wherein the signal filter parameter is a spectral parameter of the common component, and wherein the processing element:
generates the first cardiac component by filtering the first PPG signal with the first signal filter using the spectral parameter, and
generates the second cardiac component by filtering the second PPG signal with the second signal filter using the spectral parameter.

6. The electronic fitness device of claim 1, wherein the signal filter parameter is a common waveform associated with the common component and the processing element:
generates the first cardiac component by comparing the first PPG signal with the common waveform, and
generates the second cardiac component by comparing the second PPG signal with the common waveform.

7. The electronic fitness device of claim 6, further comprising a second optical transmitter positioned along the bottom wall, the second optical transmitter configured to transmit a third optical signal having a second wavelength, wherein the processing element is further configured to:
control the second optical transmitter to transmit the third optical signal during a third period of time,
receive the third PPG signal from the optical receiver, and
compare the third PPG signal with the common waveform to generate a third cardiac component, and
wherein the signal-to-noise ratio of the third PPG signal is lower than the signal-to-noise ratio of the first PPG signal.

8. The electronic fitness device of claim 1, wherein the processing element is further configured to:
determine values of a plurality of filter coefficients for each of at least a first signal filter and a second signal filter using the signal filter parameter, each signal filter being a discrete-time, multi-tap time delay line filter with each tap configured using one of the plurality of filter coefficients,
periodically update the filter coefficients based on a feedback signal based on a difference between the first cardiac component and the second PPG signal.

9. The electronic fitness device of claim 8, further comprising a second optical transmitter positioned along the bottom wall, the second optical transmitter configured to transmit a third optical signal having a second wavelength, wherein the processing element is further configured to:
control the second optical transmitter to transmit the third optical signal during a third period of time,
receive the third PPG signal from the optical receiver, and
filter the third PPG signal with a third signal filter to generate a third cardiac component.

10. The electronic fitness device of claim 1, wherein the signal filter parameter is one of a filter coefficient, a waveform associated with the identified common component, or a spectral parameter of the identified common component.

11. The electronic fitness device of claim 1, wherein the second optical signal has the first wavelength.

12. The electronic fitness device of claim 3, wherein the second optical signal has a third wavelength, the third wavelength being different than the first wavelength of the first optical signal.

* * * * *